United States Patent [19]

Ito et al.

[11] Patent Number: 5,500,422
[45] Date of Patent: Mar. 19, 1996

[54] BENZAMIDE DERIVATIVE

[75] Inventors: Yasuo Ito, Katsuyama; Hideo Kato, Fukui; Shingo Yasuda, Katsuyama; Nobuhiko Iwasaki, Katsuyama; Hiroyuki Nishino, Katsuyama; Makoto Takeshita, Katsuyama, all of Japan

[73] Assignee: Hokuriku Seiyaku Co. Ltd., Katsuyama, Japan

[21] Appl. No.: 348,808

[22] Filed: Nov. 28, 1994

Related U.S. Application Data

[62] Division of Ser. No. 104,095, Aug. 11, 1993, Pat. No. 5,395,832.

[30] Foreign Application Priority Data

Feb. 15, 1991 [JP] Japan .................................. 3-42425
Aug. 22, 1991 [JP] Japan ................................. 3-233756

[51] Int. Cl.$^6$ ...................... C07D 211/36; A61K 31/445
[52] U.S. Cl. .................... 514/212; 514/227.5; 514/238.8; 514/331; 514/428; 540/610; 544/58.4; 544/169; 546/221; 546/233; 548/146; 548/215; 548/557; 548/567
[58] Field of Search .................... 546/221, 233; 548/557, 567, 146, 215; 540/610, 606, 064; 544/58.4, 169; 514/212, 227.5, 238.8, 331, 428

[56] References Cited

U.S. PATENT DOCUMENTS 4,163,789  8/1979  Mauri et al. ............................ 546/234
4,808,624  2/1989  Monkovie et al. ..................... 514/523
4,877,780  10/1989  Vega-Noverola et al. ............. 514/161

FOREIGN PATENT DOCUMENTS 0013138    7/1980   European Pat. Off. .
099194     1/1984   European Pat. Off. .
230718     8/1987   European Pat. Off. .
243959     11/1987  European Pat. Off. .
52-122379  10/1977  Japan .
55-092834  7/1980   Japan .
58-10578   1/1983   Japan .
61-63642   4/1986   Japan .
64-50883   2/1989   Japan .

Primary Examiner—Bernard Dentz
Attorney, Agent, or Firm—Cushman, Darby & Cushman

[57] ABSTRACT

A benzamide derivative represented by the following formula:

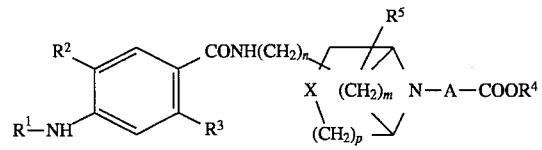

wherein $R^1$ represents a hydrogen atom or a lower alkanoyl group; $R^2$ represents a hydrogen atom or a halogen atom; $R^3$ represents a lower alkoxy group; $R^4$ represents a hydrogen atom or a lower alkyl group; $R^5$ represents a hydrogen atom, a lower alkyl group, or a lower alkoxy group; A represents $C_1$–$C_7$ alkylene group which may optionally be substituted with a lower alkyl group; X represents a methylene group, an oxygen atom, or a sulfur atom; m represents an integer of from 0 to 3; n represents an integer of from 0 to 3; and p represents an integer of from 0 to 2 and a pharmacologically acceptable salt thereof is provided. These compounds are useful since they have gastrointestinal stimulating activity, and a pharmaceutical composition comprising said compound is useful for the treatment of gastrointestinal diseases.

6 Claims, No Drawings

BENZAMIDE DERIVATIVE

This is a division of application Ser. No. 08/104,095, filed Aug. 11, 1993 which is now U.S. Pat. No. 5,395,832 which is a 371 application of PCT/JP 92/00134.

TECHNICAL FIELD

The present invention relates to novel benzamide derivatives which have excellent gastrointestinal stimulating activity and antiemetic activity and are useful as medicament for the treatment of gastrointestinal diseases. The present invention further relates to a method for preparing said benzamide derivatives and a pharmaceutical composition useful for the treatment of gastrointestinal diseases comprising said benzamide derivative as an active ingredient.

BACKGROUND ART

Since the development of Metoclopramide (The Merck Index, 11th Edition, 6063) as an antiemetic agent and a gastrointestinal prokinetic agent, various substituted benzamide derivatives having antiemetic activity and gastrointestinal stimulating activity have been provided.

For example, The Merck Index (11th edition, 2344) discloses Clebopride which is a benzamide derivative having a piperidine ring and is useful as antiulcer agent. The Merck Index (11th edition, 2318) discloses Cisapride useful as a gastrointestinal prokinetic agent. These drugs are widely used clinically. In addition, Japanese Patent Unexamined Publication No. (Sho)55-92384 discloses that benzamide derivatives substituted with an azabicyclo ring have antiemetic activity and gastrointestinal stimulating activity and that they are useful as an antiemetic agent and a gastrointestinal prokinetic agent.

However, these substituted benzamide derivatives are not sufficiently useful since they do not have stimulating activity on lower digestive tracts such as the large intestine, although they have stimulating activity on upper digestive tracts such as the stomach. Furthermore, these substituted benzamide derivatives are not satisfactory from a safe standpoint since they sometimes cause adverse reactions such as extrapyramidal syndrome or hyperprolactinemia.

Accordingly, an object of the present invention is to provide medicament for the treatment of gastrointestinal diseases having stimulating activity not only on upper digestive tract but on lower digestive tract and reduced side effects.

The inventors of the present invention conducted various studies to achieve the aforementioned object, and found that novel benzamide derivatives of the present invention have stimulating activity both on upper digestive tract and lower digestive tract. The inventors also found that these novel benzamide derivatives have reduced side effects and are useful as medicament for the treatment of gastrointestinal diseases having excellent selectivity. The present invention was achieved on the basis of these findings.

DISCLOSURE OF THE INVENTION

The present invention provides benzamide derivatives represented by the following formula (I):

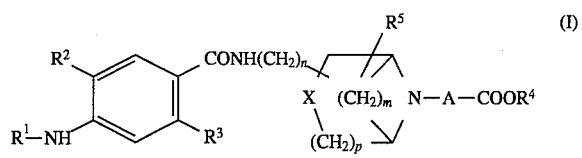

wherein, $R^1$ represents a hydrogen atom or a lower alkanoyl group; $R^2$ represents a hydrogen atom or a halogen atom; $R^3$ represents a lower alkoxy group; $R^4$ represents a hydrogen atom or a lower alkyl group; $R^5$ represents a hydrogen atom, a lower alkyl group, or a lower alkoxy group; A represents $C_1$-$C_7$ alkylene group which may optionally be substituted with a lower alkyl group; X represents a methylene group, an oxygen atom, or a sulfur atom; m represents an integer of from 0 to 3; n represents an integer of from 0 to 3; and p represents an integer of from 0 to 2, or pharmacologically acceptable salts thereof. The benzamide derivatives are useful since they have gastrointestinal stimulating activity.

According to another embodiment of the present invention, a method for preparing said benzamide derivatives is provided.

According to yet another embodiment of the present invention, a pharmaceutical composition useful for the treatment of gastrointestinal diseases which comprises said benzamide derivative as an active ingredient. The pharmaceutical composition is useful as, for example, a gastrointestinal prokinetic agent, an antiemetic agent, an agent for the treatment of irritable bowel syndrome, and agent for the treatment of constipation.

BEST MODE FOR CARRING OUT THE INVENTION

In the aforementioned formula (I), a lower alkanoyl group represented by $R^1$ may be, for example, formyl group, acetyl group, propanoyl group, butyroyl group, or trimethylacetyl group. A halogen atom represented by $R^2$ may be, for example, a fluorine atom, a chlorine atom, or a bromine atom. A lower alkoxy group represented by $R^3$ and $R^5$ may be, for example, methoxy group, ethoxy group, propoxy group, isopropoxy group, butoxy group, isobutoxy group, or tert-butoxy group. A lower alkyl group represented by $R^4$ and $R^5$ or a lower alkyl group which may optionally substitute on the alkylene group represented by A may be, for example, methyl group, ethyl group, n-propyl group, isopropyl group, n-butyl group, or tert-butyl group. $R^5$ and Ph-$CONH(CH_2)_n$— (wherein Ph represents a substituted phenyl) may substitute at any position of a ring comprising X and N.

Examples of pharmacologically acceptable salts of the benzamide drivatives of the present invention include alkali-addition salts or acid-addition salts. Examples of the alkali-addition salts include, for example, inorganic alkali-addition salts such as, for example, sodium salt, potassium salt, calcium salt, and ammonium salt, and organic base-addition salts such as, for example, ethylenediamine salt, ethanolamine salt, N,N-dialkylethanolamine salt, and triethanolamine salt. Examples of the acid addition salts include, for example, inorganic acid-addition salts such as, for example, hydrochloride, hydrobromide, hydroiodide, sulfate, nitrate, and phosphate, and organic acid-addition salts such as, for example, acetate, maleate, fumarate, citrate, oxalate, tartrate, malate, mandelate, methanesulfonate, p-toluenesulfonate, and 10-camphorsulfonate.

The benzamide derivatives of the present invention represented by the above-described formula (I) may optionally have an asymmetric carbon atom. Each of enact-isomers distinguished by the asymmetric carbon atom, an arbitrary mixture thereof, and racemate, i.e., equimolor mixture thereof, fall within the scope of the present invention. Where the benzamide derivatives of the present invention have more than one asymmetric carbon atoms, each diastereomer and an arbitrary mixture of the diastereomers also fall within the scope of the present invention.

The benzamide derivatives of the present invention may be in any one of possible conformations. For instance, where the compounds of the aforementioned formula (I) wherein p is 1, piperidine, morphorine, or thiamorphorine ring substituted with Ph-CONH(CH$_2$)$_n$— group may be in any one of configurations selected from chair form, boat form, or twist-boat form. In the specification, compounds having Ph-CONH(CH$_2$)$_n$— group and —(CH$_2$)$_m$ — cross linking group above the same side of a ring plane comprising X and N are referred to as endo-compounds, and compounds having each of the groups above the opposite sides of the plane are referred to as exo-compounds.

Preferred embodiments of the benzamide derivatives of the present invention include the following compounds:

(1) ethyl exo-[3-(4-acetylamino-2-methoxybenzamido)-8-azabicyclo[3.2.1]oct-8-yl]acetate;
(2) ethyl exo-4-[3-(4-acetylamino-2-methoxybenzamido)-8-azabicyclo[3.2.1]oct-8-yl] butyrate;
(3) ethyl endo-[3-(4-acetylamino-2-methoxybenzamido)-8-azabicyclo[3.2.1]oct-8-yl] acetate;
(4) ethyl endo-4-[3-(4-acetylamino-2-methoxybenzamido)-8-azabicyclo[3.2.1]oct-8-yl] butyrate;
(5) ethyl exo-[3-(4-acetylamino-2-methoxybenzamido)-9-azabicyclo[3.3.1]non-9-yl] acetate;
(6) ethyl exo-4-[3-(4-acetylamino-2-methoxybenzamido)-9-azabicyclo[3.3.1]non-9-yl] butyrate;
(7) ethyl endo-[3-(4-acetylamino-2-methoxybenzamido)-9-azabicyclo[3.3.1]non-9-yl] acetate;
(8) ethyl endo-3-[3-(4-acetylamino-2-methoxybenzamido)-9-azabicyclo[3.3.1]non-9-yl] propionate;
(9) ethyl endo-4-[3-(4-acetylamino-2-methoxybenzamido)-9-azabicyclo[3.3.1]non-9-yl] butyrate;
(10) ethyl endo-5-[3-(4-acetylamino-2-methoxybenzamido)-9-azabicyclo[3.3.1]non-9-yl]valerate;
(11) methyl endo-6-[3-(4-acetylamino-2-methoxybenzamido)-9-azabicyclo[3.3.1]non- 9-yl]hexanoate;
(12) methyl endo-7-[3-(4-acetylamino-2-methoxybenzamido)-9-azabicyclo[3.3.1]non- 9-yl]heptanoate;
(13) methyl endo-8-[3-(4-acetylamino-2-methoxybenzamido)-9-azabicyclo[3.3.1]non- 9-yl]octanoate;
(14) ethyl endo-[3-(4-acetylamino-2-ethoxybenzamido)-9-azabicyclo[3.3.1]non- 9-yl]acetate;
(15) ethyl endo-4-[3-(4-acetylamino-2-ethoxybenzamido)-9-azabicyclo[3.3.1]non- 9-yl]butyrate;
(16) ethyl exo-[3-(4-acetylamino-5-chloro-2-methoxybenzamido)-8-azabicyclo[3.2.1]oct- 8-yl]acetate;
(17) ethyl exo-4-[3-(4-acetylamino-5-chloro-2-methoxybenzamido)-8-azabicyclo[3.2.1]oct-8-yl]butyrate;
(18) ethyl endo-[3-(4-acetylamino-5-chloro-2-methoxybenzamido)-8-azabicyclo[3.2.1] oct-8-yl]acetate;
(19) ethyl endo-4-[3-(4-acetylamino-5-chloro-2-methoxybenzamido)-8-azabicyclo[3.2.1] oct-8-yl]butyrate;
(20) ethyl exo-[3-(4-acetylamino-5-chloro-2-methoxybenzamido)-9-azabicyclo[3.3.1] non-9-yl]acetate;
(21) ethyl exo-4-[3-(4-acetylamino-5-chloro-2-methoxybenzamido)-9-azabicyclo[3.3.1] non-9-yl]butyrate;
(22) ethyl endo-[3-(4-acetylamino-5-chloro-2-methoxybenzamido)-9-azabicyclo[3.3.1] non-9-yl]acetate;
(23) ethyl endo-3-[3-(4-acetylamino-5-chloro-2-methoxybenzamido)-9-azabicyclo[3.3.1] non-9-yl]propionate;
(24) ethyl endo-4-[3-(4-acetylamino-5-chloro-2-methoxybenzamido)-9-azabicyclo[3.3.1] non-9-yl]butyrate;
(25) ethyl endo-5-[3-(4-acetylamino-5-chloro-2-methoxybenzamido)-9-azabicyclo[3.3.1] non-9-yl]valerate;
(26) methyl endo-6-[3-(4-acetylamino-5-chloro-2-methoxybenzamido)-9-azabicyclo[3.3.1] non-9-yl]hexanoate;
(27) methyl endo-7-[3-(4-acetylamino-5-chloro-2-methoxybenzamido)-9-azabicyclo[3.3.1] non-9-yl]heptanoate;
(28) methyl endo-8-[3-(4-acetylamino-5-chloro-2-methoxybenzamido)-9-azabicyclo[3.3.1] non-9-yl]octanoate;
(29) ethyl endo-[3-(4-acetylamino-5-chloro-2-ethoxybenzamido)-9-azabicyclo[3.3.1] non-9-yl]acetate;
(30) ethyl endo-4-[3-(4-acetylamino-5-chloro-2-ethoxybenzamido)-9-azabicyclo[3.3.1]non-9-yl]butyrate;
(31) ethyl exo-[3-(4-amino-5-chloro-2-methoxybenzamido)-8-azabicyclo[3.2.1] oct-8-yl]acetate;
(32) ethyl exo-4-[3-(4-amino-5-chloro-2-methoxybenzamido)-8-azabicyclo[3.2.1] oct-8-yl]butyrate;
(33) ethyl endo-[3-(4-amino-5-chloro-2-methoxybenzamido)-8-azabicyclo[3.2.1] oct-8-yl]acetate;
(34) ethyl endo-4-[3-(4-amino-5-chloro-2-methoxybenzamido)-8-azabicyclo[3.2.1] oct-8-yl]butyrate;
(35) ethyl exo-[3-(4-amino-5-chloro-2-methoxybenzamido)-9-azabicyclo[3.3.1] non-9-yl]acetate;
(36) ethyl exo-4-[3-(4-amino-5-chloro-2-methoxybenzamido)-9-azabicyclo[3.3.1] non-9-yl]butyrate;
(37) ethyl endo-[3-(4-amino-5-chloro-2-methoxybenzamido)-9-azabicyclo[3.3.1] non-9-yl]acetate;
(38) ethyl endo-3-[3-(4-amino-5-chloro-2-methoxybenzamido)-9-azabicyclo[3.3.1] non-9-yl]propionate;
(39) ethyl endo-2-[3-(4-amino-5-chloro-2-methoxybenzamido)-9-azabicyclo[3.3.1] non-9-yl]propionate;
(40) ethyl endo-4-[3-(4-amino-5-chloro-2-methoxybenzamido)-9-azabicyclo[3.3.1] non-9-yl]butyrate;
(41) ethyl endo-5-[3-(4-amino-5-chloro-2-methoxybenzamido)-9-azabicyclo[3.3.1] non-9-yl]valerate;
(42) ethyl endo-6-[3-(4-amino-5-chloro-2-methoxybenzamido)-9-azabicyclo[3.3.1] non-9-yl]hexanoate;
(43) methyl endo-7-[3-(4-amino-5-chloro-2-methoxybenzamido)-9-azabicyclo[3.3.1] non-9-yl]heptanoate;
(44) ethyl endo-8-[3-(4-amino-5-chloro-2-methoxybenzamido)-9-azabicyclo[3.3.1] non-9-yl]octanoate;
(45) ethyl endo-[3-(4-amino-5-chloro-2-ethoxybenzamido)-9-azabicyclo[3.3.1] non-9-yl]acetate;
(46) ethyl endo-4-[3-(4-amino-5-chloro-2-ethoxybenzamido)-9-azabicyclo[3.3.1] non-9-yl]butyrate;
(47) ethyl endo-[3-[(4-amino-5-chloro-2-methoxybenzamido)methyl]-9-azabicyclo[3.3.1] non-9-yl]acetate;
(48) ethyl endo-4-[3-[(4-amino-5-chloro-2-methoxybenzamido)methyl]-9-azabicyclo[3.3.1]non-9-yl]butyrate;
(49) ethyl endo-[3-[2-(4-amino-5-chloro-2-methoxybenzamido)ethyl]-9-azabicyclo[ 3.3.1]non-9-yl]acetate;
(50) ethyl endo-4-[3-[2-(4-amino-5-chloro-2-methoxybenzamido)ethyl]-9-azabicyclo[3.3.1]non-9-yl]butyrate;
(51) ethyl endo-[3-[3-(4-amino-5-chloro-2-methoxybenzamido)propyl]-9-azabicyclo[ 3.3.1]non-9-yl]acetate;
(52) ethyl endo-4-[3-[3-(4-amino-5-chloro-2-methoxybenzamido)-propyl]-9-azabicyclo[ 3.3.1]non-9-yl]butyrate;
(53) exo-[3-(4-amino-5-chloro-2-methoxybenzamido)-8-azabicyclo[3.2.1] oct-8-yl]acetic acid;
(54) exo-4-[3-(4-amino-5-chloro-2-methoxybenzamido)-8-azabicyclo[3.2.1] oct-8-yl]butyric acid;
(55) endo-[3-(4-amino-5-chloro-2-methoxybenzamido)-8-azabicyclo[3.2.1] oct-8-yl]acetic acid;
(56) endo-4-[3-(4-amino-5-chloro-2-methoxybenzamido)-8-azabicyclo[3.2.1] oct-8-yl]butyric acid;
(57) exo-[3-(4-amino-5-chloro-2-methoxybenzamido)-9-azabicyclo[3.3.1] non-9-yl]acetic acid;

(58) exo-4-[3-(4-amino-5-chloro-2-methoxybenzamido)-9-azabicyclo[3.3.1] non-9-yl]butyric acid;
(59) endo-[3-(4-amino-5-chloro-2-methoxybenzamido)-9-azabicyclo[3.3.1] non-9-yl]acetic acid;
(60) endo-3-[3-(4-amino-5-chloro-2-methoxybenzamido)-9-azabicyclo[3.3.1] non-9-yl]propionic acid;
(61) endo-2-[3-(4-amino-5-chloro-2-methoxybenzamido)-9-azabicyclo[3.3.1] non-9-yl]propionic acid;
(62) endo-4-[3-(4-amino-5-chloro-2-methoxybenzamido)-9-azabicyclo[3.3.1] non-9-yl]butyric acid;
(63) endo-5-[3-(4-amino-5-chloro-2-methoxybenzamido)-9-azabicyclo[3.3.1] non-9-yl]valeric acid;
(64) endo-6-[3-(4-amino-5-chloro-2-methoxybenzamido)-9-azabicyclo[3.3.1] non-9-yl]hexanoic acid;
(65) endo-7-[3-(4-amino-5-chloro-2-methoxybenzamido)-9-azabicyclo[3.3.1] non-9-yl]heptanoic acid;
(66) endo-8-[3-(4-amino-5-chloro-2-methoxybenzamido)-9-azabicyclo[3.3.1] non-9-yl]octanoic acid;
(67) endo-[3-(4-amino-5-chloro-2-ethoxybenzamido)-9-azabicyclo[3.3.1] non-9-yl]acetic acid;
(68) endo-4-[3-(4-amino-5-chloro-2-ethoxybenzamido)-9-azabicyclo[3.3.1] non-9-yl]butyric acid;
(69) endo-[3-[(4-amino-5-chloro-2-methoxybenzamido)methyl]-9-azabicyclo[3.3.1] non-9-yl]acetic acid;
(70) endo-4-[3-[(4-amino-5-chloro-2-methoxybenzamido)methyl]-9-azabicyclo[ 3.3.1]non-9-yl]butyric acid;
(71) endo-[3-[2-(4-amino-5-chloro-2-methoxybenzamido)ethyl]-9-azabicyclo[3.3.1] non-9-yl]acetoc acid;
(72) endo-4-[3-[2-(4-amino-5-chloro-2-methoxybenzamido)ethyl]-9-azabicyclo[3.3.1]non-9-yl]butyric acid;
(73) endo-[3-[3-(4-amino-5-chloro-2-methoxybenzamido)propyl]-9-azabicyclo[ 3.3.1]non-9-yl]acetic acid;
(74) endo-4-[3-[3-(4-amino-5-chloro-2-methoxybenzamido)propyl]-9-azabicyclo[ 3.3.1]non-9-yl]butyric acid;
(75) ethyl [4-(4-amino-5-chloro-2-methoxybenzamido)piperidino]acetate;
(76) ethyl 2-[4-(4-amino-5-chloro-2-methoxybenzamido)piperidino]propionate;
(77) ethyl 3-[4-(4-amino-5-chloro-2-methoxybenzamido)piperidino]propionate;
(78) ethyl 4-[4-(4-amino-5-chloro-2-methoxybenzamido)piperidino]butyrate;
(79) ethyl 5-[4-(4-amino-5-chloro-2-methoxybenzamido)piperidino]valerate;
(80) methyl 6-[4-(4-amino-5-chloro-2-methoxybenzamido)piperidino]hexanoate;
(81) ethyl [4-[(4-amino-5-chloro-2-methoxybenzamido)methyl]piperidino]acetate;
(82) ethyl 4-[4-[(4-amino-5-chloro-2-methoxybenzamido)methyl]piperidino]butyrate;
(83) ethyl [4-[2-(4-amino-5-chloro-2-methoxybenzamido)ethyl]piperidino]acetate;
(84) ethyl 4-[4-[2-(4-amino-5-chloro-2-methoxybenzamido)ethyl]piperidino]butyrate;
(85) ethyl [4-[3-(4-amino-5-chloro-2-methoxybenzamido)propyl]piperidino]acetate;
(86) ethyl 4-[4-[3-(4-amino-5-chloro-2-methoxybenzamido)propyl]piperidino]butyrate;
(87) [4-(4-amino-5-chloro-2-methoxybenzamido)piperidino]acetic acid;
(88) 2-[4-(4-amino-5-chloro-2-methoxybenzamido)piperidino]propionic acid;
(89) 3-[4-(4-amino-5-chloro-2-methoxybenzamido)piperidino]propionic acid;
(90) 4-[4-(4-amino-5-chloro-2-methoxybenzamido)piperidino]butyric acid;
(91) 5-[4-(4-amino-5-chloro-2-methoxybenzamido)piperidino]valeric acid;
(92) 6-[4-(4-amino-5-chloro-2-methoxybenzamido)piperidino]hexanoic acid;
(93) [4-[(4-amino-5-chloro-2-methoxybenzamido)methyl] piperidino]acetic acid;
(94) 4-[4-[(4-amino-5-chloro-2-methoxybenzamido)methyl]piperidino]butyric acid;
(95) [4-[2-(4-amino-5-chloro-2-methoxybenzamido)ethyl] piperidino]acetic acid;
(96) 4-[4-[2-(4-amino-5-chloro-2-methoxybenzamido)ethyl]piperidino]butyric acid;
(97) [4-[3-(4-amino-5-chloro-2-methoxybenzamido)propyl] piperidino]acetic acid;
(98) 4-[4-[3-(4-amino-5-chloro-2-methoxybenzamido)propyl]piperidino]butyric acid;
(99) ethyl cis-[4-(4-amino-5-chloro-2-methoxybenzamido)-3-methoxypiperidino]acetate;
(100) ethyl trans-[4-(4-amino-5-chloro-2-methoxybenzamido)-3-methoxypiperidino]acetate;
(101) ethyl cis-4-[4-(4-amino-5-chloro-2-methoxybenzamido)-3-methoxypiperidino]butyrate;
(102) ethyl trans-4-[4-(4-amino-5-chloro-2-methoxybenzamido)-3-methoxypiperidino]butyrate;
(103) methyl cis-6-[4-(4-amino-5-chloro-2-methoxybenzamido)-3-methoxypiperidino]hexanoate;
(104) ethyl cis-[4-(4-amino-5-chloro-2-methoxybenzamido)-3-methylpiperidino]acetate;
(105) ethyl trans-[4-(4-amino-5-chloro-2-methoxybenzamido)-3-methylpiperidino]acetate;
(106) ethyl cis-4-[4-(4-amino-5-chloro-2-methoxybenzamido)-3-methylpiperidino]butyrate;
(107) ethyl trans-4-[4-(4-amino-5-chloro-2-methoxybenzamido)-3-methylpiperidino]butyrate;
(108) methyl cis-6-[4-(4-amino-5-chloro-2-methoxybenzamido)-3-methylpiperidino]hexanoate;
(109) cis-[4-(4-amino-5-chloro-2-methoxybenzamido)-3-methoxypiperidino]acetic acid;
(110) trans-[4-(4-amino-5-chloro-2-methoxybenzamido)-3-methoxypiperidino]acetic acid;
(111) cis-4-[4-(4-amino-5-chloro-2-methoxybenzamido)-3-methoxypiperidino]butyric acid;
(112) trans-4-[4-(4-amino-5-chloro-2-methoxybenzamido)-3-methoxypiperidino]butyric acid;
(113) cis-6-[4-(4-amino-5-chloro-2-methoxybenzamido)-3-methoxypiperidino]hexanoic acid;
(114) cis-[4-(4-amino-5-chloro-2-methoxybenzamido)-3-methylpiperidino]butyric acid;
(115) trans-[4-(4-amino-5-chloro-2-methoxybenzamido)-3-methylpiperidino]acetic acid;
(116) cis-4-[4-(4-amino-5-chloro-2-methoxybenzamido)-3-methylpiperidino]butyric acid;
(117) trans-4-[4-(4-amino-5-chloro-2-methoxybenzamido)-3-methylpiperidino]butyric acid;
(118) cis-6-[4-(4-amino-5-chloro-2-methoxybenzamido)-3-methylpiperidino]hexanoic acid;
(119) ethyl 2-[(4-amino-5-chloro-2-methoxybenzamido)methyl]morpholino]acetate;
(120) ethyl 4-[2-[(4-amino-5-chloro-2-methoxybenzamido)methyl]morpholino]butyrate;
(121) [2-[(4-amino-5-chloro-2-methoxybenzamido)methyl]-morpholino]acetic acid;
(122) 4-[2-[(4-amino-5-chloro-2-methoxybenzamido)methyl]-morpholino]butyric acid;
(123) ethyl [2-[(4-amino-5-chloro-2-methoxybenzamido)methyl]thiamorpholino]acetate;
(124) ethyl 4-[2[(4-amino-5-chloro-2-methoxybenzamido)methyl]thiamorpholino]butyrate;
(125) [2-[(4-amino-5-chloro-2-methoxybenzamido)methyl] thiamorpholino]acetic acid;

(126) 4-[2-[(4-amino-5-chloro-2-methoxybenzamido)methyl]thiamorpholino]butyric acid;
(127) ethyl [3-[(4-amino-5-chloro-2-methoxybenzamido)methyl]pyrrolidin-1-yl]acetate;
(128) ethyl 4-[3-[(4-amino-5-chloro-2-methoxybenzamido)methyl]pyrrolidin-1-yl]butyrate;
(129) [3-[(4-amino-5-chloro-2-methoxybenzamido)methyl]pyrrolidin-1-yl]acetic acid;
(130) 4-[3-[(4-amino-5-chloro-2-methoxybenzamido)methyl]pyrrolidin-1-yl]butyric acid;
(131) ethyl [3-(4-amino-5-chloro-2-methoxybenzamido)pyrrolidin-1-yl]acetate;
(132) ethyl 4-[3-(4-amino-5-chloro-2-methoxybenzamido)pyrrolidin-1-yl]butyrate;
(133) [3-(4-amino-5-chloro-2-methoxybenzamido)pyrrolidin-1-yl]acetic acid; and
(134) 4-[3-(4-amino-5-chloro-2-methoxybenzamido)pyrrolidin-1-yl]butyric acid. However, the present invention is not limited to these examples.

The benzamide derivative represented by formula (I) can be prepared according to a method described below which is an embodiment of the present invention. However, methods for preparing said compound are not limited to these processes.

A process for preparing the benzamide derivatives of the present invention represented by formula (I) comprises the following steps:

(a) reacting a compound represented by the following formula (II) wherein $R^1$, $R^2$, $R^3$, $R^5$, X, m, n and p are the same as those defined above:

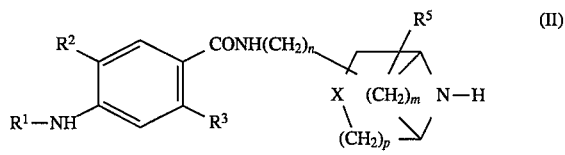

with a compound represented by the following formula (III) wherein A is the same as that defined above, , $R^6$ represents a lower alkyl and Y represents a halogen atom:

$$Y\text{-}A\text{-}CO_2R^6 \text{ or } CH{=}CH_2CO_2R^6 \qquad (III)$$

to carry out N-alkylation reaction in an organic solvent or without a solvent and in the presence or absence of a base as a dehydrohalogenating agent; and (b) halogenating or hydrolyzing the product obtained in the above step (a), if desired.

Examples of the organic solvent used for the N-alkylation in the method of the present invention include, for example, alcohols such as, for example, methanol, ethanol, n-propanol, isopropanol, and n-butanol; aromatic hydrocarbons such as, for example, benzene, toluene, and xylene; and aprotic polar solvents such as, for example, tetrahydrofuran, 1,4-dioxane, acetonitrile, N,N-dimethylformamide, N-methyl-2-pyrrolidone, and dimethyl sulfoxide. Examples of the base used include, for example, metallic sodium, sodium hydride, sodium methoxide, sodium ethoxide, sodium amide, sodium hydroxide, potassium hydroxide, sodium carbonate, potassium carbonate, sodium hydrogen carbonate, and potassium hydrogen carbonate. The reaction may be carried out at from ice-cooling temperature to refluxing temperature of a solvent.

Halogenation may be carried out by the treatment with a halogenating agent in an organic solvent. Examples of the halogenating agent used include, for example, chlorine, bromine, and sulfuryl chloride. Examples of the organic solvent used include, for example, alcohols such as, for example, methanol, ethanol, and n-propanol; halogenated hydrocarbons such as, for example, dichloromethane, chloroform, carbon tetrachloride, and 1,2-dichloroethane; and aliphatic acids such as, for example, acetic acid. The reaction may be carried out at from −30° to refluxing temperature of a solvent.

Hydrolysis may be carried out by using an acid or a base. For acidic hydrolysis, acids such as hydrochloric acid or sulfric acid may be used, and for alkaline hydrolysis, bases such as sodium hydroxide, potassium hydroxide, sodium carbonate, or potassium carbonate may be used. These acids and bases may be used in the reaction in a form of aqueous solution, or alternatively, solutions in methanol, ethanol, n-propanol, isopropanol, n-butanol, sec-butanol, or tert-butanol, or solutions in aqueous organic solvents. The reaction may be carried out at from ice-cooling temperature to refluxing temperature of a solvent.

The compounds represented by formula (II) used as starting materials in the aforementioned preparation process of the present invention are novel compounds with a few exceptions. The compounds can be prepared according to the scheme set out below, in which $R^1$, $R^2$, $R^3$, $R^5$, X, m, n, and p are the same as those defined above, $R^7$ represents a lower alkyl group, and Z represents a halogen atom. Specific examples of the preparation process are given as reference examples in Examples which follows.

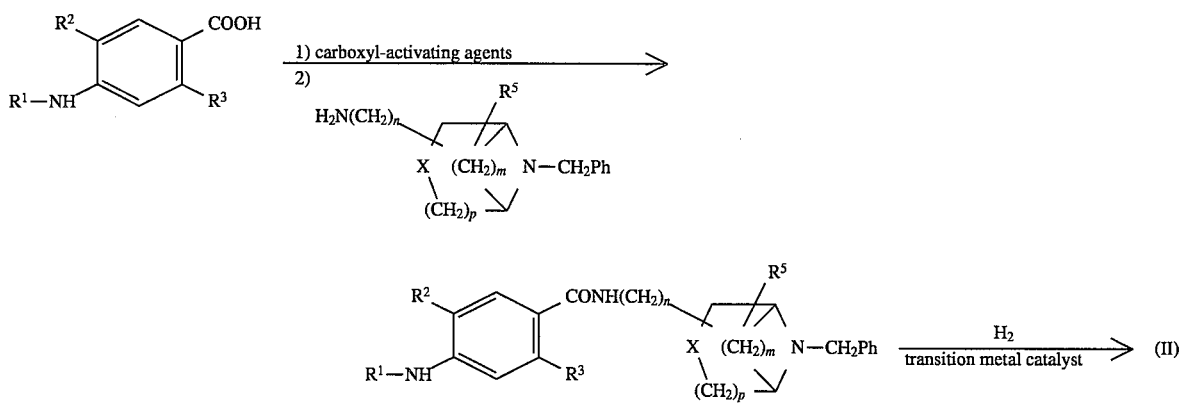

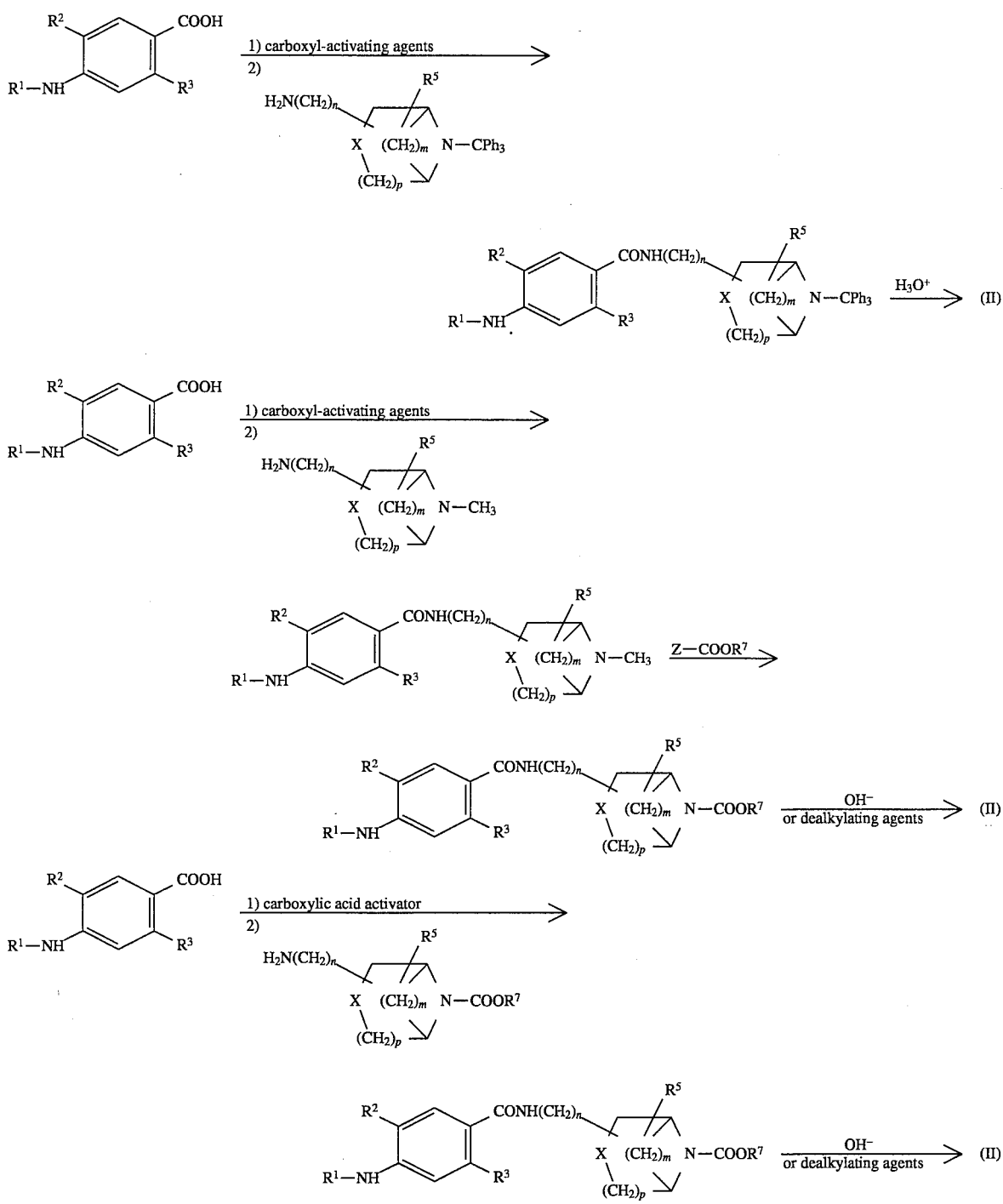

The benzamide derivatives represented by formula (I) prepared according to the process described above and their pharmacologically acceptable salts have hyderfunctional activity on digestive tract and are useful for the treatment of gastrointestinal diseases. The compounds may preferably be formulated in a pharmaceutical composition as an active ingredient. The pharmaceutical composition comprising said compound as an active ingredient may generally be formulated and administered to a patient as orally available compositions such as, for example, capsules, tablets, subtilized granules, granules, powder or syrup, or administered as injection, suppository, eye drop, eye ointment, ear drop, or topical composition.

These pharmaceutical compositions can be prepared by ordinary methods. If necessary, pharmacologically and pharmaceutically acceptable additives may be added. For the preparation of orally available compositions and suppository, excipients such as, for example, lactose, D-mannitol, cornstarch, or crystalline cellulose; disintegrants such as, for example, carboxymethylcellulose or calcium carboxymethylcellulose; binders such as, for example, hydroxypropylcellulose, hydroxypropylmethylcellulose, or polyvinylpyrrolidone; lubricants such as, for example, magnesium stearate or talc; coating agents such as, for example, hydroxypropylmethylcellulose, sucrose, or titanium oxide; or bases such as, for example polyethylene glycol or hard fat may be used as pharmaceutical additives. For the preparation of an injection, eye drop, or ear drop, solubilizing agents or solubilizers such as, for example, distilled water for injection, saline, or propylene glycol which is useful for an aqueous composition or a composition for preparing aqueous solution before use; pH adjusting agents such as, for example, an inorganic or organic acid or base; isotonicity agents such as, for example, sodium chloride, glucose, or glycerin; or stabilizers may be used as pharmaceutical additives. For the preparation of eye ointment and topical composition, suitable pharmaceutical additives ordinarily formulated in ointment, cream, or cataplasms such as white vaseline, macrogol, glycerin, or cloth may be used.

The pharmaceutical compositions of the present invention may be administered orally to an adult patient at a daily dose of about 0.1 to 500 mg. The dose may be increased or decreased depending on the age or conditions of a patient.

As an example demonstrating remarkable advantageous effects of the compounds of the present invention, experimental results are set out below relating to effects on motility of digestive tract of a conscious dog.

Effects on gastrointestinal motility in conscious dog

Under systemical anesthesia, force transducers were chronically implanted to the stomach and the colon of the adult male or female dogs in a direction to measure circular muscle contraction according to the method of Ito et al. (Japanese Journal of Smooth Muscle Research, 13, 33, 1976). A silicone tube chronically attached into jugular vein for intravenous administration of test compounds. After the animal was recovered from the operation, test compounds were administered at about two hours after feeding while gastrointestinal motility was measured. The gastrointestinal motility was indicated as motor index, and the effects of test compounds were estimated by the change of motor index for twenty minutes before and after the administration. The results are summarized in Table 1. It can be concluded that the compounds of the present invention exhibit excellent stimulating effects on lower digestive tracts as well as upper digestive tracts.

TABLE 1

Stimulating Effect on Gastrointestinal Motility (Conscious Dog)

| Test Compound | Dose (mg/kg, i.v.) | Change of Motor Index (%) | |
|---|---|---|---|
| | | Stomach | Colon |
| Example 23 | 1 | 133.5 | 133.3 |
| Example 24 | 0.1 | 116.0 | 134.8 |
| Example 25 | 1 | 180.9 | 132.7 |
| Example 27 | 0.1 | 113.4 | 134.5 |
| Example 28 | 1 | 141.5 | 163.7 |
| Example 32 | 1 | 176.7 | 158.5 |
| Example 33 | 1 | 147.1 | 117.4 |
| Example 34 | 1 | 187.0 | 191.5 |
| Example 35 | 1 | 186.8 | 135.8 |
| Example 36 | 1 | 195.9 | 119.6 |
| Example 38 | 1 | 145.6 | 140.3 |
| Example 39 | 0.1 | 134.7 | 159.1 |
| Example 41 | 1 | 118.3 | 172.0 |
| Example 43 | 1 | 166.5 | 504.8 |
| Example 46 | 1 | 182.5 | 165.6 |
| Example 58 | 0.1 | 180.7 | 217.5 |
| Example 63 | 1 | 129.6 | 156.6 |
| Example 64 | 0.1 | 200.3 | 234.5 |

The present invention will be explained by way of reference examples and examples. However, the present invention is not limited to these examples.

EXAMPLES

Reference Example 1 endo-4-Acetylamino-N-(9-azabicyclo[3.3.1]non-3-yl)-2-methoxybenzamide (1) endo-4-Acetylamino-N-(9-benzyl-9-azabicyclo[3.3.1]non-3-yl)-2-methoxybenzamide To a mixture of 11.0 g of 4-acetylamino-2-methoxybenzoic acid, 8.5 ml of triethylamine, and 210 ml of tetrahydrofuran, 5.3 ml of ethyl chloroformate was added dropwise with stirring under ice-cooling. After the mixture was stirred for 1.5 hours under ice-cooling, 12.72 g of endo-9-benzyl-9-azabicyclo[3.3.1]nonan-3-amine was added by portions. Stirring was continued for 2.5 days at room temperature, and then the mixture was concentrated under reduced pressure. Water was added to the residue, and pH was adjusted to 9 using 10% aqueous potassium carbonate solution. Crystals precipitated were collected by filtration and washed with water and then with ethanol to give 15.7 g of colorless crystals. Recrystallization from methanol gave colorless needles, m.p. 233.5°– 235° C.

Anal. $C_{25}H_{31}N_3O_3$ Calcd. C: 71.23; H: 7.41; N: 9.97 Found C: 71.19; H: 7.50; N: 9.93

(2) endo-4-Acetylamino-N-(9-azabicyclo[3.3.1]non-3-yl)-2-methoxybenzamide

To a mixture of 15.5 g of endo-4-acetylamino-N-(9-benzyl-9-azabicyclo[3.3.1]non-3-yl)- 2-methoxybenzamide, 20 ml of acetic acid, and 180 ml of methanol, 2.0 g of Pearlman's catalyst (20% palladium hydroxide on carbon) was added, and then hydrogenolysis was carried out for 1 hour at room temperature under ordinary pressure. The catalyst was removed and the filtrate was concentrated under reduced pressure. The residue was taken up in water and pH was adjusted to 9 by adding potassium carbonate. Crystals precipitated were collected by filtration and washed with water to give 12.6 g of pale yellow crystals. Recrystallization from 1,2-dichloroethane gave colorless prisms, m.p. 196°–200° C.

Anal. $C_{18}H_{25}N_3O_3 \cdot 1/4H_2O$ Calcd. C: 64.36; H: 7.65; N: 12.51 Found C: 64.32; H: 7.53; N: 12.47

In the same manner as Reference Example 1, the compounds of Reference Examples 2–4 were obtained.

Reference Example 2 exo-4-Acetylamino-N-(8-azabicyclo[3.2.1]oct-3-yl)-2-methoxybenzamide fumarate (1) exo-4-Acetylamino-N-(8-benzyl-8-azabicyclo[3.2.1]oct-3-yl)-2-methoxybenzamide Appearance: pale brown needles (MeOH)

IR Spectrum ν (KBr) cm$^{-1}$: 1694, 1668

NMR Spectrum δ (DMSO-d$_6$) ppm: 1.50–1.83(6H,m), 1.88–2.14(2H,m), 2.06(3H,s), 3.05–3.32(2H,m), 3.55(2H,s), 3.85(3H,s), 4.05– 4.29(1H,m), 7.10–7.45(5H,m) , 7.17(1H, dd,J=8.6,1.7 Hz), 7.48 (1H,d,J=1.7 Hz), 7.62–7.77(1H,m), 7.70(1H,d,J=8.6 Hz), 10.04(1H,s)

Mass Spectrum m/z: 407 (M$^+$)

(2) exo-4-Acetylamino-N-(8-azabicyclo[3.2.1]oct-3-yl)-2-methoxybenzamide fumarate Appearance: colorless crystals (MeOH)

m.p. 223°–225° C. (decomp.)

Anal. $C_{17}H_{23}N_3O_3 \cdot C_4H_4O_4$ Calcd. C: 58.19; H: 6.28; N: 9.69 Found C: 58.05; H: 6.45; N: 9.71

Reference Example 3 exo-4-Acetylamino-N-(9-azabicyclo[3.3.1]non-3-yl)-2-methoxybenzamide fumarate

(1) exo-4-Acetylamino-N-(9-benzyl-9-azabicyclo[3.3.1]non-3-yl)-2-methoxybenzamide Appearance: slightly brown needles (MeOH)

m.p. 215°–216° C. Anal. $C_{25}H_{31}N_3O_3$ Calcd. C: 71.23; H: 7.41; N: 9.97 Found C: 71.12; H: 7.48; N: 9.89

(2) exo-4-Acetylamino-N-(9-azabicyclo[3.3.1]non-3-yl)-2-methoxybenzamide fumarate Appearance: colorless crystals (MeOH)

m.p. 194°–196° (decomp.)

Anal. $C_{18}H_{25}N_3O_3 \cdot C_4H_4O_4 \cdot 3/4H_2O$ Calcd. C: 57.32; H: 6.67; N: 9.12 Found C: 57.13; H: 6.58; N: 9.12

Reference Example 4 endo-4-Acetylamino-N-(9-azabicyclo[3.3.1]non-3-yl)-2-ethoxybenzamide

(1) endo-4-Acetylamino-N-(9-benzyl-9-azabicyclo[3.3.1]non-3-yl)-2-ethoxybenzamide Appearance: colorless needles (MeOH)

m.p. 215°–216° C.

Anal. $C_{26}H_{33}N_3O_3$ Calcd. C: 71.70; H: 7.64; N: 9.65 Found C: 71.45; H: 7.61; N: 9.47

(2) endo-4-Acetylamino-N-(9-azabicyclo[3.3.1]non-3-yl)-2-ethoxybenzamide

Appearance: colorless needles ($H_2O$)

m.p. 116°–119° C.

224°–226° C.

Anal. $C_{19}H_{27}N_3O_3 \cdot 5/2H_2O$ Calcd. C: 58.44; H: 8.26; N: 10.76 Found C: 58.45; H: 7.86; N: 10.40

Reference Example 5 endo-4-Acetylamino-N-(8-azabicyclo[3.2.1]oct-3-yl)-5-chloro-2-methoxybenzamide

(1) endo-4-Acetylamino-5-chloro-2-methoxy-N-(8-methyl-8-azabicyclo[3.2.1]oct-3-yl)benzamide To a mixture of 38.0 g of 4-acetylamino-5-chloro-2-methoxybenzoic acid, 26.1 ml of triethylamine, and 500 ml of tetrahydrofuran, 15.7 ml of ethyl chloroformate was added dropwise with stirring under ice-cooling. Stirring was continued for 1 hour under ice-cooling, and then a solution of 23.0 g of endo-8-methyl-8-azabicyclo[3.2.1]octan-3-amine in 40 ml of tetrahydrofuran was added dropwise. Stirring was continued for 1.5 hours at room temperature, and then insoluble materials were removed and the filtrate obtained was concentrated under reduced pressure. Water was added to the residue and pH was adjusted to 9 by using aqueous potassium carbonate solution. Crystals precipitated were collected by filtration and Washed with water and then with ethyl acetate to give 48.6 g of slightly yellow crystals.

(2) Methyl endo-[3-(4-acetylamino-5-chloro-2-methoxybenzamido)-8-azabicyclo[3.2.1]oct-8-yl]formate To a mixture of 40.0 g of endo-4-acetylamino-5-chloro-2-methoxy-N-(8-methyl-8-azabicyclo[3.2.1]oct-3-yl)benzamide, 16.0 g of potassium carbonate, and 400 ml of chloroform, 80.0 ml of methyl chloroformate was added dropwise with stirring at room temperature. The mixture was refluxed for 19 hours, and then insoluble materials were removed and the filtrate obtained was concentrated under reduced pressure. The residue was washed with ethyl acetate and then with hot methanol to give 17.5 g of colorless crystals. Recrystallization from dichloromethane-methanol gave colorless needles, m.p. 250°–252° C.

Anal. $C_{19}H_{24}ClN_3O_5 \cdot 1/2H_2O$ Calcd. C: 54.48; H: 6.02; N: 10.03 Found C: 54.17; H: 5.77; N: 9.79

(3) endo-4-Acetylamino-N-(8-azabicyclo[3.2.1]oct-3-yl)-5-chloro-2-methoxybenzamide To a suspension of 16.3 g of methyl endo-[3-(4-acetylamino-5-chloro-2-methoxybenzamido)-8-azabicyclo[3.2.1]oct-8-yl]formate in 400 ml of dichloromethane, 22.0 ml of iodo trimethylsilane was added dropwise with stirring at room temperature. Stirring was continued for 6 hours at room temperature, and then aqueous sodium hydrosulfite solution was added. Aqueous layer was separated after pH was adjusted to 2 using 10% hydrochloric acid. The aqueous layer was basified using potassium carbonate and then extracted with dichloromethane. The extract was dried over anhydrous sodium sulfate and concentrated under reduced pressure. The residue was purified using column chromatography on aluminum oxide [eluent: dichloromethane→dichloromethane-methanol (50:1)]to afford 8.41 g of pale yellow syrup.

IR Spectrum ν (liq) $cm^{-1}$: 1694, 1644

NMR Spectrum δ ($CDCl_3$) ppm: 1.65–2.30(9H,m), 2.28(3H,s), 3.60–3.74(2H,m), 4.02(3H,s), 4.30–4.46(1H, m), 7.82(1H,br-s), 8.21(1H,s), 8.34(1H,s), 8.40–8.50(1H,m)

High Resolution Mass Spectrum: $C_{17}H_{22}ClN_3O_3$ Calcd. m/z: 351.1350, 353.1320 Found m/z: 351.1363, 353.1325

In the same manner as Reference Example 5, the compound of Reference Example 6 was obtained.

Reference Example 6 endo-4-Acetylamino-N-(9-azabicyclo[3.3.1]non-3-yl)-5-chloro-2-methoxybenzamide

(1) endo-4-Acetylamino-5-chloro-2-methoxy-N-(9-methyl-9-azabicyclo[3.3.1]non-3-yl)benzamide Appearance: slightly brown amorphous solid IR Spectrum ν (KBr) $cm^{-1}$: 1706, 1646

NMR Spectrum δ ($CDCl_3$) ppm: 1.00–1.15(2H,m), 1.20–1.40(2H,m), 1.45–1.60(1H,m), 1.85–2.10(3H,m), 2.28(3H,s), 2.40–2.75(2H,m), 2.50(3H,s), 3.00–3.15(2H,m), 3.98(3H,s), 4.35–4.60(1H,m), 7.60–7.70(1H,m), 7.82(1H, br-s), 8.21(1H,s), 8.30(1H,s)

High Resolution Mass Spectrum: $C_{19}H_{26}ClN_3O_3$ Calcd. m/z: 379.1663, 381.1633 Found m/z: 379.1654, 381.1630

(2) Methyl endo-[3-(4-acetylamino-5-chloro-2-methoxybenzamido)-9-azabicyclo[3.3.1]non-9-yl]formate Appearance: colorless crystals (AcOEt)

m.p. 202°–205° C.

Anal. $C_{20}H_{26}ClN_3O_5$ Calcd. C: 56.67; H: 6.18; N: 9.91 Found C: 56.49; H: 6.25; N: 9.69

(3) endo-4-Acetylamino-N-(9-azabicyclo[3.3.1]non-3-yl)-5-chloro-2-methoxybenzamide Appearance: pale yellow syrup IR Spectrum ν (liq) $cm^{-1}$: 1694, 1646

NMR Spectrum δ ($CDCl_3$) ppm: 1.14–2.00(8H,m), 2.18(1H,br-s), 2.28(3H,s), 2.20–2.40(2H,m), 3.30–3.47(2H, m), 3.99(3H,s), 4.06–4.28(1H,m), 7.57–7.70(1H,m), 7.81(1H,br-s), 8.22(1H,s), 8.32(1H,s)

High Resolution Mass Spectrum: $C_{18}H_{24}ClN_3O_3$ Calcd. m/z: 365.1506, 367.1477 Found m/z: 365.1510, 367.1457

Reference Example 7 endo-4-Amino-N-(8-azabicyclo[3.2.1]oct-3-yl)-5-chloro-2-methoxybenzamide hydrochloride

To a solution of 7.86 g of endo-4-acetylamino-N-(8-azabicyclo[3.2.1]oct-3-yl)-5-chloro-2-methoxybenzamide in 23 ml of ethanol, 40 ml of 32% hydrogen chloride/ethanol solution was added and then the mixture was refluxed for 5.5 hours. The reaction mixture was concentrated under reduced pressure, and the residue was washed with ethanol to give 5.05 g of pale brown crystals. Recrysttallization from methanol gave colorless needles, m.p. 280°– 282° C. (decomp.).

Anal. $C_{15}H_{20}ClN_3O_2 \cdot HCl \cdot 3/4H_2O$ Calcd. C: 50.08; H: 6.30; N: 11.68 Found C: 50.07; H: 6.20; N: 11.57

In the same manner as Reference Example 7, the compound of Reference Example 8 was obtained.

Reference Example 8 endo-4-Amino-N-(9-azabicyclo[3.3.1]non-3-yl)-5-chloro-2-methoxybenzamide hydrochloride Appearance: slightly brown needles (EtOH)
m.p. 257°–261° C. (decomp.)
Anal. $C_{16}H_{22}ClN_3O_2 \cdot HCl \cdot H_2O$ Calcd. C: 50.80; H: 6.66; N: 11.11 Found C: 50.74; H: 6.57; N: 10.91

Reference Example 9

4-Amino-5-chloro-2-methoxy-N-(4-piperidinyl)benzamide hydrochloride (1) 4-Amino-5-chloro-2-methoxy-N-(1-triphenylmethyl-4-piperidinyl)benzamide To a mixture of 16.40 g of 4-amino-5-chloro-2-methoxybenzoic acid, 13.60 ml of triethylamine, and 330 ml of dry tetrahydrofuran, 8.55 ml of ethyl chloroformate was added with stirring under ice-cooling. Stirring was continued for 2 hours under ice-cooling, 30.64 g of 4-amino-1-triphenylmethylpiperidine was added by portions. After stirring was continued for 20 hours at room temperature, insoluble materials were removed and the filtrate obtained was concentrated under reduced pressure. The residue was dissolved in dichloromethane and washed with water. The solution was dried over anhydrous sodium sulfate and then concentrated under reduced pressure. The residue was washed with n-hexane to give 39.42 g of colorless crystals.

IR Spectrum ν (KBr) cm$^{-1}$: 1646, 1624

NMR Spectrum δ (CDCl$_3$) ppm: 1.57–1.81(2H,m), 1.92–2.19(2H,m), 2.73–3.38(2H,m), 3.58–4.08(3H,m), 4.33(2H,br-s), 6.25(1H,s), 7.05– 7.55(15H,m), 7.67(1H,br-s), 8.06(1H,s)

(2) 4-Amino-5-chloro-2-methoxy-N-(4-piperidinyl)benzamide hydrochloride

A mixture of 39.42 g of 4-amino-5-chloro-2-methoxy-N-(1-triphenylmethyl-4-piperidinyl)benzamide, 10 ml of concentrated hydrochloric acid, and 600 ml of acetone was refluxed for 40 minutes. After the mixture was cooled to 5° C., crystals precipitated were collected by filtration and washed with acetone to give 25.79 g of colorless crystals, m.p. 165°–168° C.

IR Spectrum ν (KBr) cm$^{-1}$: 2948, 2812, 1640

NMR Spectrum δ (DMSO-d$_6$) ppm: 1.63–1.85(2H,m), 1.92–2.13(2H,m), 2.88–3.09(2H,m), 3.13–3.33(2H,m), 3.83(3H,s), 3.88–4.07(1H,m), 6.53(1H,s), 7.62(1H,s), 7.66–7.79(1H,m)

Mass Spectrum m/z: 283, 285 (3:1) [M$^+$ (free base)]

In the same manner as Reference Example 9, the compounds of Reference Examples 10 and 11 were obtained.

Reference Example 10

4-Amino-5-chloro-2-methoxy-N-[(2-morpholinyl)-methyl]benzamide hydrochloride (1) 4-Amino-5-chloro-2-methoxy-N-[(4-triphenylmethyl-2-morpholinyl)-methyl]benzamide Appearance: slightly brown crystals NMR Spectrum δ (CDCl$_3$) ppm: 1.35–1.80(2H,m), 2.80–3.10(2H,m), 3.10–3.35(1H,m), 3.50–3.75(1H,m), 3.71(3H,s), 3.75–4.10(3H,m), 4.35(2H,br-s), 6.23(1H,s), 7.05–7.60(15H,m), 7.80–7.90(1H,m), 8.07(1H,s)

(2) 4-Amino-5-chloro-2-methoxy-N-[(2-morpholinyl)methyl]benzamide hydrochloride

Appearance: slightly brown crystals (H$_2$O)
m.p. 219°–222° C.
Anal. $C_{13}H_{18}ClN_3O_3 \cdot HCl \cdot H_2O$ Calcd. C: 44.08; H: 5.98; N: 11.86 Found C: 44.20; H: 5.88; N: 11.82

Reference Example 11

4-Amino-5-chloro-2-methoxy-N-[(3-pyrrolidinyl)methyl]benzamide hydrochloride (1) 4-Amino-5-chloro-2-methoxy-N-[(1-triphenylmethyl-3pyrrolidinyl)methyl]benzamide Appearance: slightly brown crystals NMR Spectrum δ (CDCl$_3$) ppm: 1.33–1.50(1H,m), 1.50–1.65(1H,m), 1.76–1.96(1H,m), 2.10–2.40(3H,m), 2.46–2.50(1H,m), 3.30–3.60(2H,m), 3.77(3H,s), 4.35(2H, br-s), 6.26(1H,s), 7.05–7.60(15H,m), 7.60– 7.75(1H,m), 8.10(1H,s)

(2) 4-Amino-5-chloro-2-methoxy-N-[(3-pyrrolidinyl)methyl]benzamide hydrochloride Appearance: pale yellow crystals (H$_2$O)
m.p. 204°–206° C.
Anal. $C_{13}HClN_3O_2 \cdot HCl \cdot 5/4H_2O$ Calcd. C: 45.56; H: 6.32; N: 12.26 Found C: 45.60; H: 6.14; N: 12.30

Reference Example 12 cis-4-Amino-5-chloro-2-methoxy-N-[(3-methoxy-4-piperidinyl)benzamide (1) Ethyl cis-[4-(4-amino-5-chloro-2-methoxybenzamido)-3-methoxypiperidino]formate To a mixture of 33.3 g of 4-amino-5-chloro-3-methoxybenzoic acid, 27.0 ml of triethylamine, and 450 ml of tetrahydrofuran, 16.2 ml of ethyl chloroformate was added dropwise with stirring under ice-cooling. Stirring was continued for 1.5 hours under ice-cooling, a solution of 35.0 g of ethyl cis-(4-amino-3-methoxypiperidino)formate in 50 ml of tetrahydrofuran was added dropwise. After being stirred for 20 hours at room temperature, the reaction mixture was concentrated under reduced pressure. Water was added to the residue, and the mixture was extracted with dichloromethane. The extract was washed with aqueous potassium carbonate solution, dried over anhydrous sodium sulfate, and then concentrated under reduced pressure. The residue was washed with diethyl ether to give 44.5 g of colorless crystals.

(2) cis-4-Amino-5-chloro-2-methoxy-N-[(3-methoxy-4-piperidinyl) benzamide

A mixture of 44.0 g of ethyl cis-[4-(4-amino-5-chloro-2-methoxybenzamide)-3-methoxypiperidino] formate, 67.7 g of potassium hydroxide, and 400 ml of iso-propanol was refluxed for 9 hours. The reaction mixture was concentrated under reduced pressure, and then water was added to the residue and the mixture was extracted with dichloromethane. The extract was dried over anhydrous sodium sulfate and then concentrated under reduced pressure. The residue was washed with iso-propylether to give 27.0 g of colorless crystals. Recrystallization from ethanol gave colorless prisms, m.p. 193°–194° C.

Anal. $C_{14}H_{20}ClN_3O_3$ Calcd. C: 53.59; H: 6.42; N: 13.39 Found C: 53.44; H: 6.38; N: 13.28

Example 1

Ethyl endo-[3-(4-acetylamino-2-methoxybenzamido)-9-azabicyclo[3.3.1]non-9-yl]acetate A mixture of 12.4 g of endo-4-acetylamino-N-(9-azabicyclo[3.3.1]non-3-yl)-2-methoxybenzamide, 4.6 ml of ethyl bromoacetate, 5.72 g of potassium carbonate, and 75 ml of N,N-dimethylformamide was heated for 2 hours at 60° C. with stirring. The reaction mixture was poured into ice-water, and crystals precipitated were collected by filtration and washed with water to give 13.4 g of pale yellow crystals. Recrystallization from benzene gave colorless prisms, m.p. 85°–88° C.

Anal. $C_{22}H_{31}N_3O_5 \cdot 1/2H_2O$ Calcd. C: 61.95; H: 7.56; N: 9.85 Found C: 61.85; H: 7.55; N: 9.86

In the same manner as Example 1, the compounds of Examples 2 to 12 were obtained.

Example 2

Ethyl endo-4-[3-(4-acetylamino-2-methoxybenzamido)-9-azabicyclo[3.3.1]non-9-yl]butyrate Appearance: colorless oil IR Spectrum ν (liq) cm$^{-1}$: 1732, 1698, 1638

NMR Spectrum δ (CDCl$_3$) ppm: 1.00–2.15(10H,m), 1.26(3H,t,J=7.0 Hz), 2.21(3H,s), 2.37(2H,t,J=7.0Hz), 2.45–2.60(2H,m), 2.60–2.85(2H,m), 3.10–3.30 (2H,m), 3.96(3H,s), 4.13(2H,q,J=7.0Hz), 4.30–4.55(1H,m), 6.77(1H,dd,J=8.5,1.5 Hz), 7.65–7.75(1H,m), 7.82(1H,s), 7.86(1H,d,J=1.5 Hz), 8.09(1H,d,J=8.5 Hz)

High Resolution Mass Spectrum: $C_{24}H_{35}N_3O_5$ Calcd. m/z: 445.2577 Found m/z: 445.2586

Example 3

Methyl endo-6-[3-(4-acetylamino-2-methoxybenzamido)-9-azabicyclo[3.3.1]non-9-yl]hexanoate Appearance: colorless oil IR Spectrum ν (liq) cm$^{-1}$: 1738, 1698, 1638

NMR Spectrum δ (CDCl$_3$) ppm: 1.00–2.00(14H,m), 2.21(3H,s), 2.33(2H,t,J=7.5 Hz), 2.40–2.65(2H,m), 2.65–2.85(2H,m), 3.15–3.35(2H,m), 3.67(3H,s), 3.97(3H,s), 4.40–4.60(1H,m), 6.78(1H,d,J=8.0 Hz), 7.65–7.70(1H,m), 7.70–7.80(1H,m), 7.85(1H,s), 8.10(1H,d,J=8.0 Hz)

High Resolution Mass Spectrum: $C_{25}H_{37}N_3O_5$ Calcd. m/z: 459.2733 Found m/z: 459.2744

Example 4

Methyl endo-8-[3-(4-acetylamino-2-methoxybenzamido)-9-azabicyclo[3.3.1]non-9-yl]octanoate Appearance: colorless needles (EtOH)

m.p. 159°–160° C.

IR Spectrum ρ (KBr) cm$^{-1}$: 1740, 1696, 1636

NMR Spectrum δ (CDCl$_3$) ppm: 1.00–2.15(18H,m), 2.21(3H,s), 2.30(2H,t,J=7.5 Hz), 2.40–2.60(2H,m), 2.60–2.70(2H,m), 3.10–3.30(2H,m), 3.67(3H,s), 3.95(3H,s), 4.30–4.60(1H,m), 6.80(1H,dd,j=8.5,2.0 Hz), 7.65–7.75(1H,m), 7.87(1H,m), 8.07(1H,d,J=8.5 Hz), 8.26(1H,d,J=2.0 Hz)

High Resolution Mass Spectrum: $C_{27}H_{41}N_3O_5$ Calcd. m/z: 487.3046 Found m/z: 487.3041

Example 5

Ethyl endo-3-[3-(4-acetylamino-2-methoxybenzamido)-9-azabicyclo[3.3.1]non-9-yl]propionate Appearance: colorless oil IR Spectrum ν (KBr) cm$^{-1}$: 1732, 1698, 1638

NMR Spectrum δ (CDCl$_3$) ppm : 1.00–2.06(8H,m), 1.27(3H,t,J=7.0 Hz), 2.21(3H,s), 2.32–2.54(2H,m), 2.40(2H,t,J=7.0 Hz), 2.95(2H,t,J=7.0 Hz), 3.06–3.20(2H, m), 3.95(3H,s), 4.15(2H,q,J=7.0 Hz), 4.28–4.46(1H,m), 6.77 (1H,dd,J=8.5,2.0 Hz), 7.58–7.72(1H,m) , 7.87(1H,br-s) , 8.06(1H,d,J=8.5 Hz), 8.19(1H,s)

High Resolution Mass Spectrum: $C_{23}H_{33}N_3O_5$ Calcd. m/z: 431.2420 Found m/z: 431.2420

Example 6

Ethyl endo-5-[3-(4-acetylamino-2-methoxybenzamido)-9-azabicyclo[3.3.1]non-9-yl]valerate Appearance: colorless oil IR Spectrum ν (KBr) cm$^{-1}$: 1734, 1696, 1636

NMR Spectrum δ (CDCl$_3$) ppm: 0.95–2.10(12H,m), 1.26(3H,t,J=7.0 Hz), 2.21(3H,s), 2.31(2H,t,J=7.0 Hz), 2.37–2.55(2H,m), 2.64(2H,t,J=7.0 Hz), 3.03–3.20(2H,m), 3.95(3H,s), 4.13(2H,q,J=7.0 Hz), 4.33–4.53(1H,m), 6.77(1H,dd,J=8.5,2.0 Hz), 7.58–7.72(1H,m), 7.87(1H,d,J=2.0 Hz), 8.07(1H,d,J=8.5 Hz), 8.09(1H,s)

High Resolution Mnass Spectrum: $C_{25}H_{37}N_3O_5$ Calcd. m/z: 459.2733 Found m/z: 459.2724

Example 7

Methyl endo-7-[3-(4-acetylamino-2-methoxybenzamido)-9-azabicyclo[3.3.1]non-9-yl] heptanoate Appearance: colorless oil IR Spectrum ν (KBr) cm$^{-1}$: 1732, 1696, 1644

NMR Spectrum δ (CDCl$_3$) ppm: 1.00–2.10(16H,m), 2.21(3H,s), 2.30(2H,t,J=7.5 Hz), 2.37–2.55(2H,m), 2.61(2H,t,J=7.0 Hz), 3.05– 3.20(2H,m), 3.66(3H,s), 3.93(3H,s), 4.35–4.55(1H,m), 6.84 (1H,dd,J=8.5,1.5 Hz), 7.64–7.78(1H,m), 7.87(1H,d,J=8.5 Hz), 8.03(1H,d,J=8.5 Hz), 8.85(1H,s)

High Resolution Mass Spectrum: $C_{26}H_{39}N_3O_5$ Calcd. m/z: 473.2890 Found m/z: 473.2893

Example 8

Ethyl endo-[3-(4-acetylamino-2-ethoxybenzamido)-9-azabicyclo[3.3.1]non-9-yl]acetate Appearance: colorless needles (benzene)
m.p. 77°–81° C.
Anal. $C_{23}H_{33}N_3O_5 \cdot 1/2H_2O$ Calcd. C: 62.71;,H: 7.78; N: 9.54 Found C: 62.72; H: 7.57; N: 9.55

Example 9

Ethyl exo-[3-(4-acetylamino-2-methoxybenzamido)-9-azabicyclo[3.3.1]non-9-yl]acetate Appearance: colorless oil
IR Spectrum ν (KBr) cm$^{-1}$: 1746, 1686, 1636
NMR Spectrum δ (CDCl$_3$) ppm: 1.28(3H,t,J=7.0 Hz), 1.40–2.13(10H,m), 2.20(3H,s), 3.00–3.15(2H,m), 3.54(2H,s), 3.94(3H,s), 4.19(2H,q,J=7.0 Hz), 4.80–5.00(1H,m), 6.78(1H,dd,J=8.5,2.0 Hz), 7.57–7.75(1H,m), 7.83(1H,d,J=2.0 Hz), 7.87(1H,s), 8.09(1H,d,J=8.5 Hz)
High Resolution Mass Spectrum: $C_{22}H_{31}N_3O_5$ Calcd. m/z: 417.2264 Found m/z: 417.2253

Example 10

Ethyl exo-[3-(4-acetylamino-2-methoxybenzamido)-8-azabicyclo[3.2.1]oct-8-yl]acetate Appearance: pale yellow oil
IR Spectrum δ (KBr) cm$^{-1}$: 1746, 1692, 1638
NMR Spectrum ν (CDCl$_3$) ppm: 1.28(3H,t,J=7.0 Hz), 1.60–2.10(8H,m), 2.20(3H,s), 3.23(2H,s), 3.30–3.45(2H,m), 3.92(3H,s), 4.20(2H,q,J=7.0 Hz), 4.28–4.48(1H,m), 6.77(1H,dd,J=8.5, 2.0 Hz), 7.60(1H,s), 7.60–7.80(1H,m), 7.80(1H,d,J=2.0 Hz), 7.80(1H,s), 8.10(1H,d,J=8.5 Hz)
High Resolution Mass Spectrum: $C_{21}H_{29}N_3O_5$ Calcd. m/z: 403.2107 Found m/z: 403.2111

Example 11

Ethyl endo-3-[3-(4-acetylamino-5-chloro-2-methoxybenzamido )-8-azabicyclo[3.2.1]oct-8-yl]acetate Appearance: colorless prisms (EtOH)
m.p. 144°–145° C.
Anal. $C_{21}H_{28}ClN_3O_5$ Calcd. C: 57.60; H: 6.44; N: 9.60 Found C: 57.45; H: 6.32; N: 9.49

Example 12

Ethyl endo-4-[3-(4-amino-5-chloro-2-methoxybenzamido)-8-azabicyclo[3.2.1]oct-8-yl]butyrate Appearance: pale brown needles (AcOEt)
m.p. 154°–156° C.
Anal. $C_{21}H_{30}ClN_3O_4 \cdot 1/4H_2O$ Calcd. C: 58.87; H: 7.18; N: 9.81 Found C: 58.80; H: 6.97; N: 9.71

Example 13

Ethyl endo-[3-(4-acetylamino-5-chloro-2-methoxybenzamido)-9-azabicyclo[3.3.1]non-9-yl]acetate To a suspension of 13.0 g of ethyl endo-[3-(4-acetylamino-2-methoxybenzamido)-9-azabicyclo[3.3.1] non-9-yl]acetate in 140 ml of dichloromethane, 3.4 ml of sulfuryl chloride was added dropwise at –10° C. Stirring was continued at room temperature for 1.5 hours, and then the mixture was made basic by adding saturated aqueous sodium bicarbonate solution. The organic layer was separated and dried over anhydrous sodium Sulfate. After being concentrated under reduced pressure, the residue was purified by column chromatography on silica gel (eluent: dichloromethane-methanol/50:1) to give 11.4 g of pale yellow amorphous solid.
IR Spectrum ν (KBr) cm$^{-1}$: 1750, 1646
NMR Spectrum δ (CDCl$_3$) ppm: 1.05–2.17(8H,m), 1.28(3H,t,J=7.3 Hz), 2.28(3H,s), 2.42–2.64(2H,m), 3.12–3.34(2H,m), 3.49(2H,s), 3.98(3H, 4.17(2H,q,J=7.3 Hz), 4.34–4.55(1H,m), 7.58–7.71(1H,m), 7.80(1H,s), 8.22(1H,s), 8.32(1H,s)
High Resolution Mass Spectrum: $C_{22}H_{30}ClN_3O_5$ Calcd. m/z: 451.1874, 453.1844 Found m/z: 451.1859, 453.1853
In the same manner as Example 13, the compounds of Examples 14 to 22 were obtained.

Example 14

Ethyl endo-4-[3-(4-acetylamino-5-chloro-2-methoxybenzamido)-9-azabicyclo[3.3.1]non-9-yl]butyrate Appearance: colorless oil
IR Spectrum ν (liq) cm$^{-1}$: 1732, 1704, 1646
NMR Spectrum δ (CDCl$_3$) ppm: 1.00–2.10(10H,m), 1.27(3H,t,J=7.0 Hz), 2.28(3H,s), 2.37(2H,t,J=7.5 Hz), 2.45–2.60(2H,m), 2.65–2.80(2H,m), 3.05–3.20(2H,m), 3.98(3H,s), 4.14(2H,q,J=7.0 Hz), 4.30–4.50(1H,m), 7.55–7.65(1H,m), 7.82(1H,s), 8.20(1H,s), 8.31(1H,s)
High Resolution Mass Spectrum: $C_{24}H_{34}ClN_3O_5$ Calcd. m/z: 479.2187, 481.2157 Found m/z: 479.2190, 481.2173

Example 15

Methyl endo-6-[3-(4-acetylamino-5-chloro-2-methoxybenzamido )-9-azabicyclo[3.3.1] non-9-yl]hexanoate fumarate Appearance: colorless needles (EtOH)
m.p. 157°–161° C.
Anal. $C_{25}H_{36}ClN_3O_5 \cdot C_4H_4O_4 \cdot 5/4H_2O$ Calcd. C: 55.06; H: 6.77; N, 6.64 Found C: 54.95; H: 6.94; N, .6.72

Example 16

Methyl endo-8-[3-(4-acetylamino-5-chloro-2-methoxybenzamido )-9-azabicyclo[3.3.1] non-9-yl]octanoate Appearance: colorless needles (EtOH )
IR Spectrum ν (KBr) cm$^{-1}$ : 1738, 1704, 1646

NMR Spectrum δ (CDCl₃) ppm: 1.00–2.10(18H,m), 2.28(3H,s), 2.31(2H,t,J=7.5 Hz), 2.35–2.55(2H,m), 2.55–2.75(2H,m), 3.10–3.25(2H,m), 3.67(3H,s), 3.98(3H,s), 4.30–4.55(1H,m), 7.55–7.75(1H,m), 7.81(1H,s), 8.21(1H,s), 8.31(1H,s)

High Resolution Mass Spectrum: $C_{27}H_{40}ClN_3O_5$ Calcd. m/z: 521.2657, 523.2627 Found m/z: 521.2642, 523.2617

Example 17

Ethyl endo-3-[3-(4-acetylamino-5-chloro-2-methoxybenzamido)-9-azabicyclo[3.3.1]non-9-yl]propionate sesquifumarate Appearance: colorless needles (EtOH)

m.p. 170°–172° C.

Anal. $C_{23}H_{32}ClN_3O_5 \cdot 3/2 C_4H_4O_4$ Calcd. C: 54.42; H: 5.98; N: 6.56 Found C: 54.18; H: 6.06; N: 6.69

Example 18

Ethyl endo-5-[3-(4-acetylamino-5-chloro-2-methoxybenzamido)-9-azabicyclo[3.3.1]non-9-yl]valerate fumarate Appearance: colorless crystals (acetone)

m.p. 127°–129° C.

Anal. $C_{25}H_{36}ClN_3O_5 \cdot C_4H_4 \cdot 1/2 H_2O$ Calcd. C: 56.26; H: 6.67; N: 6.79 Found C: 56.34; H: 6.72; N: 6.65

Example 19

Methyl endo-7-[3-(4-acetylamino-5-chloro-2-methoxybenzamido)-9-azabicyclo[3.3.1]non-9-yl]heptanoate fumarate Appearance: colorless needles (MeOH-Et₂O)

m.p. 124.5°–126° C.

Anal. $C_{26}H_{38}ClN_3O_5 \cdot C_4H_4O_4 \cdot 3/4 H_2O$ Calcd. C: 56.51; H: 6.88; N: 6.59 Found C: 56.51; H: 6.82; N: 6.59

Example 20

Ethyl endo-[3-(4-acetylamino-5-chloro-2-ethoxybenzamido)-9-azabicyclo[3.3.1]non-9-yl]acetate Appearance: slightly yellow syrup IR Spectrum ν (liq) cm⁻¹: 1748, 1704, 1646

NMR Spectrum δ (CDCl₃) ppm: 1.05–1.64(5H,m), 1.75–2.10(3H,m), 2.45–2.65(2H,m), 1.28(3H,t,J=7.0 Hz), 1.52(3H,t,J=7.0 Hz), 2.27(3H,s), 3.16–3.31(2H,m), 3.49(2H,s), 4.18(2H,q,J=7.0 Hz), 4.22(2H,q,J=7.0 Hz), 4.37–4.55(1H,m), 7.78(1H,br-s), 7.80–7.94(1H,m), 8.21(1H,s), 8.27(1H,s)

High Resolution Mass Spectrum: $C_{23}H_{32}ClN_3O_5$ Calcd. m/z: 465.2031, 467.2001 Found m/z: 465.2033, 467.2003

Example 21

Ethyl exo-[3-(4-acetylamino-5-chloro-2-methoxybenzamido)-9-azabicyclo[3.3.1]non-9-yl]acetate 1/2 fumarate Appearance: colorless needles (MeOH)

IR Spectrum ν (KBr) cm⁻¹: 1738, 1698, 1638

NMR Spectrum δ (DMSO-d₆) ppm: 1.19(3H,t,J=7.0 Hz), 1.43–2.05(10H,m), 2.14(3H,s), 2.90–3.00(2H,m), 3.48(2H,s), 3.85(3H,s), 4.08(2H,q,J=7.0 Hz), 4.55–4.73(1H,m), 6.61(1H,s), 7.69(1H,s), 7.73(1H,s), 7.70–7.90(1H,m), 9.42(1H,s)

High Resolution Mass Spectrum: $C_{22}H_{30}ClN_3O_5$ Calcd. m/z: 451.1874, 453.1844 Found m/z: 451.1876, 453.1840

Example 22

Ethyl exo-[3-(4-acetylamino-5-chloro-2-methoxybenzamido)-8-azabicyclo[3.2.1]oct-8-yl]acetate maleate Appearance: colorless crystals (EtOH)

m.p. 174°–175° C.

Anal. $C_{21}H_{28}ClN_3O_5 \cdot C_4H_4O_4$ Calcd. C: 54.20; H: 5.82; N: 7.58 Found C: 54.03; H: 5.85; N: 7.56

Example 23

Ethyl endo-[3-(4-amino-5-chloro-2-methoxybenzamido)-9-azabicyclo[3.3.1]non-9-yl]acetate To a solution of 11.0 g of ethyl endo-[3-(4-acetylamino-5-chloro-2-methoxybenzamido)-9-azabicyclo[3.3.1]non-9-yl]acetate in 22 ml of ethanol, 66 ml of 20% hydrogen chloride/ethanol solution was added and the mixture was refluxed for 1 hour. The reaction mixture was concentrated under reduced pressure, and then the residuce was dissolved in water and pH was adjusted to 10 with potassium carbonate. Crystals precipitated were collected by filtration and washed with water and then with isopropyl ether to give 8.88 g of pale brown crystals. Recrystallization from ethanol gave colorless crystals, m.p. 163.5°–164.5° C.

Anal. $C_{20}H_{28}ClN_3O_4$ Calcd. C: 58.60; H: 6.88; N: 10.25 Found C: 58.39; H: 6.84; N: 10.26

In the same manner as Example 23, the compounds of Examples 24 to 33 were obtained.

Example 24

Ethyl endo-4-[3-(4-amino-5-chloro-2-methoxybenzamido)-9-azabicyclo[3.3.1]non-9-yl]butyrate Appearance: pale orange prisms (EtOH)

m.p. 136.5°–138° C.

Anal. $C_{24}H_{36}ClN_3O_4$ Calcd. C: 60.33; H: 7.36; N: 9.59 Found C: 60.27; H: 7.41; N: 9.52

Example 25

Ethyl endo-6-[3-(4-amino-5-chloro-2-methoxybenzamido)-9-azabicyclo[3.3.1]non-9-yl]hexanoate Appearance: colorless prisms (EtOH)

m.p. 122°–123.5° C.

Anal. $C_{24}H_{36}ClN_3O_4$ Calcd. C: 61.86; H: 7.79; N: 9.02 Found C: 61.68; H: 7.80; N: 9.01

Example 26

Ethyl endo-8-[3-(4-amino-5-chloro-2-methoxybenzamido)-9-azabicyclo[3.3.1] non-9-yl]octanoate Appearance: colorless needles (EtOH)

m.p. 108°–109° C.

Anal. $C_{26}H_{40}ClN_3O_4$ Calcd. C: 63.21; H: 8.16; N: 8.50 Found C: 62.93; H: 8.14; N: 8.46

Example 27

Ethyl endo-3-[3-(4-amino-5-chloro-2-methoxybenzamido)-9-azabicyclo[3.3.1] non-9-yl]propionate Appearance: pale pink needles (AcOEt)

m.p. 110°–112° C.

Anal. $C_{21}CH_{30}ClN_3O_4$ Calcd. C: 59.50; H: 7.13; N: 9.91 Found C: 59.31; H: 7.12; N: 9.89

Example 28

Ethyl endo-5-[3-(4-amino-5-chloro-2-methoxybenzamido)-9-azabicyclo[3.3.1] non-9-yl]valerate Appearance: colorless crystals (EtOH)

m.p. 126°–128° C.

Anal. $C_{23}H_{34}ClN_3O_4$ Calcd. C: 61.12; H: 7.58; N: 9.30 Found C: 60.85; H: 7.49; N: 9.26

Example 29

Methyl endo-7-[3-(4-amino-5-chloro-2-methoxybenzamido)-9-azabicyclo[3.3.1]non- 9-yl]heptanoate Appearance: colorless prisms (MeOH-Et₂O)

m.p. 144.5°–145.5° C.

Anal. $C_{24}H_{36}ClN_3O_4$ Calcd. C: 61.86; H: 7.79; N: 9.02 Found C: 61.64; H: 7.75; N: 9.06

Example 30

Ethyl endo-[3-(4-amino-5-chloro-2-ethoxybenzamido)-9-azabicyclo[3.3.1] non-9-yl]acetate Appearance: colorless needles (EtOH)

m.p. 215°–217° C.

Anal. $C_{21}H_{30}ClN_3O_4$ Calcd. C: 59.50; H: 7.13; N: 9.91 Found C: 59.26; H, 7.04; N: 9.87

Example 31

Ethyl exo-[3-(4-amino-5chloro-2-methoxybenzamido)-9-azabicyclo[3.3.1] non-9-yl]acetate Appearance: pale pink crystals (iso-PrOH-Et₂O)

m.p. 161°–164° C.

Anal. $C_{20}H_{28}ClN_3O_4 \cdot 3/4H_2O$ Calcd. C: 56.73; H: 7.02; N: 9.92 Found C: 56.73; H: 6.63; N: 9.96

Example 32

Ethyl endo-[3-(4-amino-5-chloro-2-methoxybenzamido)-8-azabicyclo[3.2.1] oct-8-yl]acetate Appearance: colorless plates (EtOH)

m.p. 187°–188° C.

Anal. $C_{19}H_{26}ClN_3O_4$ Calcd. C: 57.65; H: 6.62; N: 10.61 Found C: 57.57; H: 6.52; N: 10.42

Example 33

Ethyl exo-[3-(4-amino-5-chloro-2-methoxybenzamido)-8-azabicyclo[3.2.1] oct-8-yl]acetate Appearance: pale orange prisms (EtOH-Et₂O)

m.p. 188.5°–190° C.

Anal. $C_{19}H_{26}ClN_3O_4$ Calcd. C: 57.65; H: 6.62; N: 10.61 Found C: 57.60; H: 6.57; N: 10.49

Example 34 endo-[3-(4-Amino-5-chloro-2-methoxybenzamido)-9-azabicyclo[3.3.1]non- 9-yl]acetic acid hydrochloride To a suspension of 8.00 g of ethyl endo-[3-(4-amino-5-chloro-2-methoxybenzamido)-9-azabicyclo[ 3.3.1]non-9-yl]acetate in 80 ml of methanol, 19.5 ml of 2N sodium, hydroxide solution was added and the mixture was refluxed for 1 hour. After the reaction mixture was concentrated under reduced pressure, the residuce was dissolved in a small volume of water and pH was adjusted to 1 with 10% hydrochloric acid. Crystals precipitated were collected by filtration, washed with water, and then recrystallized from methanol-isopropyl ether to give 5.75 g of colorless powder, m.p. 189°–194° C. (decomp.).

Anal. $C_{18}H_{24}ClN_3O_4 \cdot HCl \cdot H_2O$ Calcd. C: 49.55; H: 6.23; N: 9.63 Found C: 49.38; H: 5.99; N: 9.49

In the same manner as Example 34, the compounds of Examples 35 to 45 were obtained.

Example 35 endo-4-[3-(4-Amino-5-chloro-2-methoxybenzamido)-9-azabicyclo[3.3.1]non-9-yl] butyric acid hydrochloride Appearance: colorless crystals (H₂O)

m.p. 166°–167° C.

Anal. $C_{20}H_{28}ClN_3O_4 \cdot HCl \cdot 3/2H_2O$ Calcd. C: 50.74; H: 6.81; N: 8.88 Found C: 50.68; H: 6.66; N: 8.91

Example 36 endo-6-[3-(4-Amino-5-chloro-2-methoxybenzamido)-9-azabicyclo[3.3.1]non-9-yl]hexanoic acid hydrochloride Appearance: colorless crystals (H₂O)

m.p. 237°–239° C.

Anal. $C_{22}H_{32}ClN_3O_4 \cdot HCl \cdot 5/4H_2O$ Calcd. C: 53.17; H: 7.20; N: 8.46 Found C: 53.32; H: 7.01; N: 8.48

Example 37 endo-8-[3-(4-Amino-5-chloro-2-methoxybenzamido)-9-azabicyclo[3.3.1]non- 9-yl]octanoic acid hydrochloride Appearance: slightly orange crystals ($H_2O$)
m.p. 125°–128° C.
Anal. $C_{24}H_{36}ClN_3O_4 \cdot HCl 5/4H_2O$ Calcd. C: 54.91; H: 7.58; N: 8.00 Found C: 54.87; H: 7.44; N: 7.98

Example 38 endo-3-[3-(4-Amino-5-chloro-2-methoxybenzamido)-9-azabicyclo[3.3.1]non- 9-yl]propionic acid hydrochloride Appearance: pale brown prisms ($H_2O$)
m.p. 157°–160° C.
Anal. $C_{19}H_{26}ClN_3O_4 \cdot HCl .7/4H_2O$ Calcd. C: 49.20; H: 6.63; N: 9.06 Found C: 49.27; H: 6.41; N: 9.07

Example 39 endo-5-[3-(4-Amino-5-chloro-2-methoxybenzamido)-9-azabicyclo[3.3.1] non-9-yl]valeric acid hydrochloride Appearance: pale pink crystals ($H_2O$)
m.p. 152°–153.5° C
Anal. $C_{21}H_{30}ClN_3O_4 \cdot HCl .7/4H_2O$ Calcd. C: 51.27; H: 7.06; N: 8.54 Found C: 51.30; .H: 6.89; N: 8.53

Example 40 endo-7-[3-(4-Amino-5-chloro-2-methoxybenzamido)-9-azabicyclo[3.3.1]non- 9-yl]heptanoic acid hydrochloride Appearance: colorless needles ($H_2O$)
m.p. 130°–133° C.
Anal. $C_{23}H_{34}ClN_3O_4 \cdot HCl .2H_2O$ Calcd. C: 52.67; H: 7.49; N: 8.01 Found C: 52.61; H: 7.21; N: 8.14

Example 41 endo-[3-(4-Amino-5-chloro-2-ethoxybenzamido)-9-azabicyclo[3.3.1] non-9-yl]acetic acid hydrochloride Appearance: slightly yellow needles ($H_2O$)
m.p. 216°–220° C. (decomp.)
Anal. $C_{19}H_{26}ClN_3O_4 \cdot HCl .5/2H_2O$ Calcd. C: 47.80; H: 6.76; N: 8.80 Found C: 48.05; H: 6.41; N: 8.93

Example 42 exo-[3-(4-Amino-5-chloro-2-methoxybenzamido)-9-azabicyclo[3.3.1]non-9-yl]acetic acid Appearance: pale orange crystals (MeOH)
m.p. 250°–252° C. (decomp.)
Anal. $C_{18}H_{24}Cl N_3O_4 \cdot 3/4H_2O$ Calcd. C: 54.68; H: 6.50; N: 10.63 Found C: 54.68; H: 6.25; N: 10.94

Example 43 endo-[3-(4-Amino-5-chloro-2-methoxybenzamido)-8-azabicyclo[3.2.1]oct-8-yl] acetic acid hydrochloride Appearance: slightly yellow needles ($H_2O$)
m.p. 254°–256° C. (decomp.)
Anal. $C_{17}H_{22}ClN_3O_4 \cdot HCl .3/2H_2O$ Calcd. C: 47.34;, H: 6.08; N: 9.74 Found C:, 47.36; H: 5.96; N: 9.79

Example 44 endo-4-[3-(4-Amino-5-chloro-2-methoxybenzamido)-8-azabicyclo[3.2.1]oct- 8-yl]butyric acid hydrochloride Appearance: colorless crystals ($H_2O$)
m.p. 242°–243° C.
Anal. $C_{19}H_{26}ClN_3O_4 HCl .5/4H_2O$ Calcd. C: 50.17; H: 6.54; N: 9.24 Found C: 50.29; H: 6.38; N: 9.23

Example 45 exo-[3-(4-Amino-5-chloro-2-methoxybenzamido)-8-azabicyclo[3.2.1] oct-8-yl]butyric acid Appearance: pale orange crystals (MeOH-$Et_2O$)
m.p. 273°–276° C. (decomp.)
Anal. $C_{17}H_{22}ClN_3O_4$ Calcd. C: 55.51; H: 6.03; N: 11.42 Found C: 55.20; H: 6.05; N: 11.20

Example 46

Ethyl [4-(4-amino-5-chloro-2-methoxybenzamido)-piperidino]acetate hydrochloride

A mixture of 3.20 g of 4-amino-5-chloro-2-methoxy-N-(4-piperidinyl)benzamide hydrochloride, 1.22 ml of ethyl bromoacetate, 3.04 g of porassium carbonate, and 32 ml of N,N-dimethylformamide was stirred for 2.5 hours with heating at 60° C. The reaction mixture was concentrated under reduced pressure, and then the residue was added with water and extracted with dichloromethane. The extract was washed with saturated aqueous sodium chloride solution, dried over anhydrous sodium sulfate, and then concentrated under reduced pressure to give brown oil. The result was converted to the hydrochloride by an ordinary method to afford 3.31 g of pale yellow crystals. Recrystallization from ethanol gave colorless plates, m.p. 196.5°–198.5° C.

Anal. $C_{17}H_{24}ClN_3O_4$ HCl Calcd. C: 50.25; H: 6.20; N: 10.34 Found C: 49.98; H: 6.23; N: 10.36

In the same manner as Example 46, the compounds of Examples 47–57 were obtained.

Example 47

Ethyl 4-[4-(4-amino-5-chloro-2-methoxybenzamido)piperidino]butyrate hydrochloride Appearance: slightly brown columns (EtOH)
m.p. 188.5°–191.5° C.
Anal. $C_{19}H_{28}ClN_3O_4 \cdot HCl$ Calcd. C: 52.54; H: 6.73; N: 9.67 Found C: 52.18; H: 6.66; N: 9.75

Example 48

Methyl 6-[4-(4-amino-5-chloro-2-methoxybenzamido)piperidino]hexanoate hydrochloride Appearance: slightly brown needles (MeOH)
m.p. 208.5°–210.5° C.
Anal. $C_{20}H_{30}ClN_3O_4 \cdot HCl \cdot 5/4H_2O$ Calcd. C: 51.01; H: 7.17; N: 8.92 Found C: 51.06; H: 7.03; N: 8.99

Example 49

Ethyl 3-[4-(4-amino-5-chloro-2-methoxybenzamido)piperidino]propionate

Appearance: colorless needles (acetone-$Et_2O$)
m.p. 116°–117.5° C.
Anal. $C_{18}H_{26}ClN_3O_4$ Calcd. C: 56.32; H: 6.83; N: 10.95 Found C: 56.28; H: 6.74; N: 10.87

Example 50

Ethyl 5-[4-(4-amino-5-chloro-2-methoxybenzamido)piperidino]valerate hydrochloride Appearance: colorless crystals (EtOH)
m.p. 202°–203.5° C.
Anal. $C_{20}H_{30}ClN_3O_4 \cdot HCl \cdot 1/4H_2O$ Calcd. C: 53.04; H: 7.01; N: 9.28 Found C: 52.99; H: 6.95; N: 9.21

Example 51

Ethyl 2-[4-(4-amino-5-chloro-2-methoxybenzamido)piperidino]propionate fumarate

Appearance: slightly yellow crystals (EtOH)
m.p. 158°–159° C.
Anal. $C_{18}H_{26}ClN_3O_4 \cdot C_4H_4O_4$ Calcd. C: 52.85; H: 6.05; N: 8.40 Found C: 52.67; H: 5.94; N: 8.39

Example 52

Ethyl cis-[4-(4-amino-5-chloro-2-methoxybenzamido)-3-methoxypiperidino]acetate hydrochloride Appearance: colorless needles (MeOH)
m.p. 225°–226° C.
Anal. $C_{18}H_{26}ClN_3O_5 \cdot HCl \cdot 1/4H_2O$ Calcd. C: 49.04; H: 6.29; N: 9.53 Found C: 48.89; H: 6.14; N: 9.44

Example 53

Ethyl cis-4-[4-(4-amino-5-chloro-2-methoxybenzamido)-3-methoxypiperidino]butyrate hydrochloride Appearance: colorless crystals (EtOH)
m.p. 218°–219.5° C.
Anal. $C_{20}H_{30}ClN_3O_5 \cdot HCl$ Calcd. C: 51.73; H: 6.73; N: 9.05 Found C: 51.45; H: 6.64; N: 8.98

Example 54

Ethyl cis-6-[4-(4-amino-5-chloro-2-methoxybenzamido)-3-methoxypiperidino]hexanoate hydrochloride Appearance: colorless crystals (EtOH)
m.p. 207°–208.5° C.
Anal. $C_{22}H_{34}ClN_3O_5 \cdot HCl \cdot 1/4H_2O$ Calcd. C: 53.17; H: 7.20; N: 8.46 Found C: 52.95; H: 7.09; N: 8.35

Example 55

Ethyl [2-[(4-amino-5-chloro-2-methoxybenzamido)methyl]morpholino]acetate hydrochloride Appearance: pale yellow crystals ($H_2O$)
m.p. 203°–204° C.
Anal. $C_{17}H_{24}ClN_3O_5 \cdot HCl$ Calcd. C: 48.35; H: 5.97; N: 9.95 Found C: 48.12; H: 6.03; N: 9.75

Example 56

Ethyl 4-[2-[(4-amino-5-chloro-2-methoxybenzamido)methyl]morpholino]butyrate hydrochloride Appearance: pale yellow crystals (EtOH)
m.p. 196°–197° C.
Anal. $C_{19}H_{28}ClN_3O_5 \cdot HCl \cdot 1/2H_2O$ Calcd. C: 49.68; H: 6.58; N: 9.15 Found C: 49.59; H: 6.65; N: 9.10

Example 57

Ethyl [3[(4-amino-5-chloro-2-methoxybenzamido)methyl]pyrrolidin-1-yl]acetate

Appearance: pale yellow oil
IR Spectrum ν (liq.) cm$^{-1}$: 1744, 1632
NMR Spectrum δ ($CDCl_3$) ppm: 1.27(3H,t,J=7.0 Hz), 1.46–1.69(1H, m), 1.93–2.14(1H,m), 2.38–2.99(5H,m), 3.24–3.54(4H,m), 3.89(3H,s), 4.18(2H,q,J=7.0 Hz), 4.39(2H,br-s), 6.29(1H,s), 7.81(1H,br-s), 8.09(1H,s) High Resolution Mass Spectrum: $C_{17}H_{24}ClN_3O_4$ Calc. m/z : 369.1455, 371.1426 Found m/z: 369.1466, 371.1439

Example 58

[4-[(4-Amino-5-chloro-2-methoxybenzamido)piperidino]acetic acid hydrochloride

To a suspension of 2.23 g of ethyl [4-[(4-amino-5-chloro-2-methoxybenzamido)piperidino]acetate in 22 ml of methanol, 9,86 ml of 2N sodium hydroxide solution was added and the mixture was refluxed for 1 hour. After methanol was removed by distillation under reduced pressure, 10% hydrochloric acid was added to the residue and pH was adjusted to 2. After the mixture was cooled to 5° C., crystals precipitated were collected by filtration and washed with water to give 1.47 g of pale brown crystals. Recrystallization from water gave pale yellow prisms, m.p. 248°–251° C. (decomp.).
Anal. $C_{15}H_{20}ClN_3O_4 \cdot HCl \cdot 1/4H_2O$ Calcd. C: 47.07; H: 5.66; N: 10.98 Found C: 47.34; H: 5.58; N: 11.08

In the same manner as Example 58, the compounds of Examples 59–68 were obtained.

Example 59

4-[4-(4-Amino-5-chloro-2-methoxybenzamido)piperidino]butyric acid hydrochloride

Appearance: pale yellow prisms (H$_2$O)

m.p. 228.5°–231.5° C.

Anal. C$_{17}$H$_{24}$ClN$_3$O$_4$·HCl·H$_2$O Calcd. C: 48.12; H: 6.41; N: 9.90 Found C: 47.97; H: 6.34; N: 10.12

Example 60

6-[4-(4-Amino-5-chloro-2-methoxybenzamido)piperidino]hexanoic acid hydrochloride Appearance: slightly brown prisms (H$_2$O)

m.p. 223°–225° C.

Anal. C$_{19}$H$_{28}$ClN$_3$O$_4$·HCl·H$_2$O Calcd. C: 50.45; H: 6.91; N: 9.29 Found C: 50.33; H: 6.84; N: 9.25

Example 61

3-[4-(4-Amino-5-chloro-2-methoxybenzamido)piperidino]propionic acid hydrochloride Appearance: colorless needles (H$_2$O)

m.p. 218°–219.5° C.

Anal. C$_{16}$H$_{22}$ClN$_3$O$_4$·HCl Calcd. C: 48.99; H: 5.91; N: 10.71 Found C: 48.80; H: 5.84; N: 10.68

Example 62

5-[4-(4-Amino-5-chloro-2-methoxybenzamido)piperidino]valeric acid hydrochloride

Appearance: colorless crystals (H$_2$O)

m.p. 226°–227.5° C.

Anal. C$_{18}$H$_{26}$ClN$_3$O$_4$·HCl·H$_2$O Calcd. C: 49.32; H: 6.67; N: 9.59 Found C: 49.18; H: 6.45; N: 9.54

Example 63

2-[4-(4-Amino-5-chloro-2-methoxybenzamido)piperidino]propionic acid

Appearance: pale yellow crystals (H$_2$O)

m.p. 246°–247° C.

Anal. C$_{16}$H$_{22}$ClN$_3$O$_4$·5/4H$_2$O Calcd. C: 50.79; H: 6.53; N: 11.11 Found C: 50.59; H: 6.25; N: 11.06

Example 64 cis-[4-(4-Amino-5-chloro-2-methoxybenzamido)-3-methoxypiperidino]acetic acid

Appearance: colorless needles (H$_2$O)

m.p. 230°–233° C. (decomp.)

Anal. C$_{16}$H$_{22}$ClN$_3$O$_5$·5/2H$_2$O Calcd. C: 46.10; H: 6.53; N: 10.08 Found C: 46.18; H: 6.57; N: 10.00

Example 65 cis-4-[4-(4-Amino-5-chloro-2-methoxybenzamido)-3-methoxypiperidino]butyric acid hydrochloride Appearance: colorless needles (H$_2$O)

m.p. 232°–234.5° C. (decomp.)

Anal. C$_{18}$H$_{26}$ClN$_3$O$_5$·HCl·1/4H$_2$O Calcd. C: 49.04; H: 6.29; N: 9.53 Found C: 49.03; H: 6.19; N: 9.77

Example 66 cis-6-[4-(4-Amino-5-chloro-2-methoxybenzamido)-3-methoxypiperidino]hexanoic acid hydrochloride Appearance: colorless prisms (H$_2$O)

m.p. 232.5°–235.5° C. (decomp.)

Anal. C$_{20}$H$_{30}$ClN$_3$O$_5$·HCl Calcd. C: 51.73; H: 6.73; N: 9.05 Found C: 51.52; H: 6.62; N: 8.90

Example 67

[2-[(4-Amino-5-chloro-2-methoxybenzamido)methyl]morpholino]acetic acid

Appearance: slightly yellow crystals (MeOH)

m.p. 208°–210° C.

Anal. C$_{15}$H$_{20}$ClN$_3$O$_5$ Calcd. C: 50.35; H: 5.63; N: 11.74 Found C: 50.04; H: 5.53; N: 11.63

Example 68

4-[2-[(4-Amino-5-chloro-2-methoxybenzamido)methyl]morpholino]butyric acid

Appearance: colorless needles (EtOH)

m.p. 194°–195° C

Anal. C$_{17}$H$_{24}$ClN$_3$O$_5$ Calcd. C: 52.92; H: 6.27; N: 10.89 Found C: 52.60; H: 6.09; N: 10.83

| Formulation 1 | |
|---|---|
| Compound of Example 23 | 5 mg |
| Lactose | suitable amount |
| Cornstarch | 15 mg |
| Magnesium Stearate | 1 mg |
| | 80 mg |
| Formulation 2 | |
| Compound of Example 23 | 5 mg |
| Lactose | suitable amount |
| Cornstarch | 15 mg |
| Magnesium Stearate | 1 mg |
| Hydroxypropylmethylcellulose | 4 mg |
| Polyethylene glycol 6000 | 0.5 mg |
| Titanium Oxide | 0.5 mg |
| | 100 mg |
| Formulation 3 | |
| Compound of Example 23 | 10 mg |
| Lactose | suitable amount |
| D-mannitol | 500 mg |
| Hydroxypropylcellulose | 20 mg |
| Talc | 2 mg |
| | 1,000 mg |

-continued

Formulation 4

| Compound of Example 23 | 5 mg |
|---|---|
| Citric Acid | 0.5 mg |
| Glucose | 50 mg |
| Sodium Hydroxide | suitable amount |
| Distilled Water for Injection | suitable amount |
| | 1 ml |

Formulation 5

| Compound of Example 23 | 5 mg |
|---|---|
| Hard Fat | 1,295 mg |
| | 1,300 mg |

INDUSTRIAL APPLICABILITY

As explained above, the novel benzamide derivatives of the present invention represented by formula (I) have excellent gastrointestinal stimulating activity and antiemetic activity and thus are useful for the treatment of gastrointestinal diseases.

What is claimed is:

1. A benzamide derivative represented by the following formula:

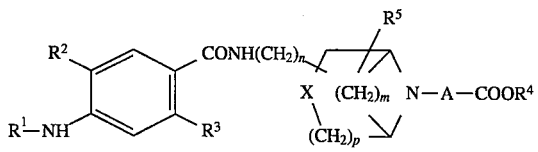

wherein, $R^1$ represents a hydrogen atom or a lower alkanoyl group; $R^2$ represents a hydrogen atom or a halogen atom; $R^3$ represents a lower alkoxy group; $R^4$ represents a hydrogen atom or a lower alkyl group; $R^5$ represents a hydrogen atom, a lower alkyl group, or a lower alkoxy group; A represents $C_1-C_7$ alkylene group which may optionally be substituted with a lower alkyl group; X represents a methylene group, an oxygen atom, or a sulfur atom; m represents an integer of n represents an integer of from 0 to 3; and p represents an integer of from 0 to 2, and a pharmacologically acceptable salt thereof.

2. Ethyl [4-(4-amino-5-chloro-2-methoxybenzamido)piperidino]acetate and a pharmacologically acceptable salt thereof.

3. [4-(4-amino-5-chloro-2-methoxybenzamido)piperidino]acetic acid and a pharmacologically acceptable salt thereof.

4. A pharmaceutical composition comprising a benzamide derivative represented by the following formula:

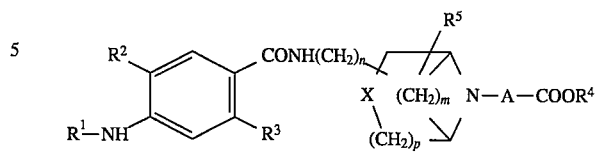

wherein $R^1$ represents a hydrogen atom or a lower alkanoyl group; $R^2$ represents a hydrogen atom or a halogen atom; $R^3$ represents a lower alkoxy group; $R^4$ represents a hydrogen atom or a lower alkyl group; $R^5$ represents a hydrogen atom, a lower alkyl group, or a lower alkoxy group; A represents $C_1-C_7$ alkylene group which may optionally be substituted with a lower alkyl group; X represents a methylene group, an oxygen atom, or a sulfur atom; m represents an integer of 0; n represents an integer of from 0 to 3; and p represents an integer of from 0 to 2 or a pharmacologically acceptable salt thereof as an active ingredient.

5. The composition according to claim 4, which is useful for the treatment of gastrointestinal diseases.

6. A method for treatment of gastrointestinal diseases comprising the step of administering to a patient an effective amount of a benzamide derivative represented by the following formula:

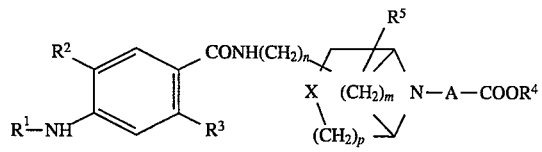

wherein $R^1$ represents a hydrogen atom or a lower alkanoyl group; $R^2$ represents a hydrogen atom or a halogen atom; $R^3$ represents a lower alkoxy group; $R^4$ represents a hydrogen atom or a lower alkyl group; $R^5$ represents a hydrogen atom, a lower alkyl group, or a lower alkoxy group; A represents $C_1-C_7$ alkylene group which may optionally be substituted with a lower alkyl group; X represents a methylene group, an oxygen atom, or a sulfur atom; m represents an integer of 0; n represents an integer of from 0 to 3; and p represents an integer of from 0 to 2 or a pharmacologically acceptable salt thereof.

* * * * *

UNITED STATES PATENT AND TRADEMARK OFFICE
CERTIFICATE OF CORRECTION

PATENT NO. : 5,500,422

DATED : March 19, 1996

INVENTOR(S) : ITO

It is certified that error appears in the above-identified patent and that said Letters Patent is hereby corrected as shown below:

On the title page, under item [30], Foreign Application Priority Data, insert the following: --February 12, 1992     PCT/JP92/00134--.(3rd entry)

Signed and Sealed this

Twentieth Day of August, 1996

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,500,422

DATED : March 19, 1996

INVENTOR(S) : Ito et al.

It is certified that error appears in the above-identified patent and that said Letters Patent is hereby corrected as shown below:

In Column 18, line 66, change " 7.87(1H,d,J=8.5 Hz)" to read —7.87(1H,d,J=1.5 Hz)—.

Signed and Sealed this

Twenty-fifth Day of March, 1997

*Attest:*

BRUCE LEHMAN

*Attesting Officer*       Commissioner of Patents and Trademarks

UNITED STATES PATENT AND TRADEMARK OFFICE
CERTIFICATE OF CORRECTION

PATENT NO. : 5,500,422

DATED : March 19, 1996

INVENTOR(S) : ITO et al.

It is certified that error appears in the above-identified patent and that said Letters Patent is hereby corrected as shown below:

Column 2, line 67, change "enact-isomers" to --enantio-isomers--

Column 4, line 57, change "zamido)-propyl]" to --zamido)propyl--

Column 6, line 61, change "ethyl]-morpholino]butyric acid" to --ethyl]morpholino]butyric acid--

Column 7, line 37, change "above, , $R^6$" to --above, $R^6$--

Column 7, line 38, change "a lower alkyl and" to --a lower alkyl, and--

Column 13, line 27, change "71.70;.H:" to --71.70; H:--

Column 13, line 56, change "and Washed" to --washed--

UNITED STATES PATENT AND TRADEMARK OFFICE
CERTIFICATE OF CORRECTION

PATENT NO. : 5,500,422
DATED : March 19, 1996
INVENTOR(S) : ITO et al.

It is certified that error appears in the above-identified patent and that said Letters Patent is hereby corrected as shown below:

Column 16, line 7, change "2-morpholinyl)-methyl]benzamide" to --2-morpholinyl)methyl]benzamide--

Column 16, line 18, change "5.98;IN: 11.86" to --5.98; N:11.86--

Column 16, line 26, change "3pyrrolidinyl)methyl]benzamide" to --3-pyrrolidinyl--

Column 16, line 37, change "$C_{13}HClN_3O_2$" to --$C_{13}H_{18}ClN_3O_2$--

Column 19, line 37, change "$\delta$" to --$\nu$--.

Column 19, line 38, change "$\nu$" to --$\delta$--

Column 20, line 14, change "sodium Sulfate" to --sodium sulfate--

Column 20, line 22, change "3.98(3H" to --3.98(3H,s)--

UNITED STATES PATENT AND TRADEMARK OFFICE
CERTIFICATE OF CORRECTION

PATENT NO. : 5,500,422
DATED : March 19, 1999
INVENTOR(S) : ITO et al.

Page 3 of 5

It is certified that error appears in the above-identified patent and that said Letters Patent is hereby corrected as shown below:

Column 20, line 46, change "$C_{24}H_{34}Cln_3O_5$" to --$C_{24}H_{34}ClN_3O_5$--

Column 20, line 58, change "N, .6.72" to --N, 6.72--

Column 21, line 17, change "$C_{23}H_{32}ClN_3O_53/2C_4H_4O_4$" to --$C_{23}H_{32}ClN_3O_5.3/2C_4H_4O_4$--

Column 21, line 28, change "$C_{25}H_{36}ClN_3O_5.C_4H_4.1/2H_2O$" to --$C_{25}H_{36}ClN_3O_5.C_4H_4O_4.1/2H_2O$--

Column 22, line 54, change "$C_{24}H_{36}ClN_3O_4$" to --$C_{22}H_{32}ClN_3O_4$--

UNITED STATES PATENT AND TRADEMARK OFFICE
CERTIFICATE OF CORRECTION

PATENT NO.   : 5,500,422                              Page 4 of 5
DATED        : March 19, 1999
INVENTOR(S)  : ITO et al.

It is certified that error appears in the above-identified patent and that said Letters Patent is hereby corrected as shown below:

Column 23, line 4, change "-9-" to -- -9- --

Column 23, line 20, change "$C_{21}CH_{30}ClN_3O_4$" to --$C_{21}H_{30}ClN_3O_4$--

Column 24, line 32, change "sodium" to --Sodium--

Column 25, line 9, change "$C_{24}H_{36}ClN_3O_4.HC15/4H_2O$" to --$C_{24}H_{36}ClN_3O_4.HCl.5/4H_2O$--

Column 25, line 34, change "C: 51.30;.H:" to --C: 51.30; H:--

Column 26, line 9, change "47.34;, H:" to --47.34; H:--

UNITED STATES PATENT AND TRADEMARK OFFICE
CERTIFICATE OF CORRECTION

PATENT NO. : 5,500,422
DATED : March 19, 1999
INVENTOR(S) : ITO et al.

Page 5 of 5

It is certified that error appears in the above-identified patent and that said Letters Patent is hereby corrected as shown below:

Column 26, line 10, change "C:, 47.36;" to --C: 47.36;--

Column 26, line 20, change "$C_{19}H_{26}ClN_3O_4HC1.5/4H_2O$" to --$C_{19}H_{26}ClN_3O_4.HCl.5/4H_2O$--

Column 26, line 39, change "of-3.20 g" to --of 3.20 g--

Column 26, line 52, change "$C_{17}H_{24}ClN_3O_4\ HCl$" to --$C_{17}H_{24}ClN_3O_4.HCl$--

Column 28, line 9, change "$C_{22}H_{34}ClN_3O_5HC1.1/4H_2O$" to --$C_{22}H_{34}ClN_3O_5.HCl.1/4H_2O$--

Column 28, line 35, change "Ethyl [3[(4-amino-" to --Ethyl [3-[(4-amino- --

Column 31, line 41, change "an integer of" to --an integer of 0;--

Signed and Sealed this

Seventeenth Day of October, 2000

*Attest:*

Q. TODD DICKINSON

*Attesting Officer*   *Director of Patents and Trademarks*